United States Patent [19]

Clark et al.

[11] Patent Number: 5,284,935

[45] Date of Patent: * Feb. 8, 1994

[54] MHC-MEDIATED TOXIC CONJUGATES USEFUL IN AMELIORATING AUTOIMMUNITY

[75] Inventors: Brian R. Clark, Redwood City; Somesh D. Sharma, Los Altos; L. Bernard Lerch, Menlo Park, all of Calif.

[73] Assignee: Anergen, Inc., Redwood City, Calif.

[*] Notice: The portion of the term of this patent subsequent to Jul. 14, 2009 has been disclaimed.

[21] Appl. No.: 635,840

[22] Filed: Dec. 28, 1990

Related U.S. Application Data

[63] Continuation-in-part of Ser. No. 576,084, Aug. 30, 1990, Pat. No. 5,130,297, which is a continuation of Ser. No. 210,594, Jun. 23, 1988, abandoned, and a continuation-in-part of Ser. No. 367,751, Jun. 21, 1989, Pat. No. 5,194,425.

[51] Int. Cl.$^5$ .......................... C07K 1/10; C07K 1/14; C07K 1/04
[52] U.S. Cl. ................................. 530/403; 530/395; 530/806; 530/807; 530/868; 424/88
[58] Field of Search .............. 530/300, 395, 402, 403, 530/806, 807, 868, 412, 413, 414; 514/2, 8; 424/88

[56] References Cited

U.S. PATENT DOCUMENTS

| | | |
|---|---|---|
| 4,199,565 | 3/1979 | Fullerton . |
| 4,400,376 | 8/1983 | Sanderson ............................. 424/88 |
| 4,478,823 | 10/1984 | Sanderson ............................. 424/88 |
| 4,675,382 | 11/1985 | Murphy . |
| 4,681,760 | 7/1987 | Fathman ............................... 424/85 |
| 4,714,759 | 12/1985 | Whitaker . |
| 4,762,915 | 1/1985 | Kung et al. . |
| 5,130,297 | 7/1992 | Sharma et al. ........................... 514/8 |
| 5,194,425 | 3/1993 | Sharma et al. ........................... 514/8 |

FOREIGN PATENT DOCUMENTS

| | | |
|---|---|---|
| 88/00057 | 1/1988 | PCT Int'l Appl. . |
| 89/12458 | 12/1989 | PCT Int'l Appl. . |
| 90/14835 | 12/1990 | PCT Int'l Appl. . |

OTHER PUBLICATIONS

H. Binz et al., J. Exp. Med. (Nov. 1979) vol. 150:1084–1097. "Binding of purified, soluble MHC polypeptide chains into isolated TCR's".
J. McCluskey et al., J. Immunology 141:1451-55 (Sep. 1988), "T cell activation by purified soluble class I MHC molecules—requirement for polyvalency".
Doyle, C. et al. Nov. 1987 Nature 330:256 "Interaction between CD4 . . . "
Golding, H. et al. Oct. 1985 Nature 317:425 "T-cell recognition . . . "
W. E. Paul (ed) *Fund. Immunol.* 1989 Raven Press pp. 69–73, 506–507.
Babbitt, B. P. et al. (1985) *Nature* 317: 359–361.
Bjorkman, P. J. et al. (1987) *Nature* 329: 506–512.
Bjorkman, P. J. et al. (1987) *Nature* 329: 512–518.
Buus, S. et al. (1987) *Science* 235: 1353–1358.
Diener, E. et al. (1986) *Science* 231: 148–150.

(List continued on next page.)

*Primary Examiner*—Christine M. Nucker
*Assistant Examiner*—T. Cunningham
*Attorney, Agent, or Firm*—Townsend and Townsend Khourie and Crew

[57] ABSTRACT

The invention is directed to methods and materials useful in treating autoimmune diseases. The therapeutic agents are of the formula X—MHC—peptide or MHc—peptide—X wherein X represents a functional moiety selected from a toxin and a labeling group; MHC is an effective portion of the MHC glycoprotein, said glycoprotein dissociated from the cell surface on which it normally resides; and "peptide" represents an antigenic peptide sequence associated with an autoantigen;—represents a covalent bond or a linker bound to X and MHC or to X and peptide by covalent bonds; and—represents a covalent bond, a noncovalent association, or a linker covalently bound to or associated with the MHC and peptide. These complexes can be used to target helper T-cells which are specifically immunoreactive with autoantigens.

8 Claims, 24 Drawing Sheets

OTHER PUBLICATIONS

Killen, J. A. et al. (1984) *J. Immunol.* 133: 2549-2553.
Livingstone, A. M. et al. (1987) *Ann. Rev. Immunol.* 5: 477-501.
Marx, J. L. (1987) *Science* 238: 613-614.
Puri, J. et al. (1980) *Eur. J. Immunol.* 10: 273-281.
Rennie, D. P. et al. (1983) *The Lancet* (Dec. 10) 1338-1340.
Sterz, R. K. M. et al. (1985) *J. Immunol.* 134: 841-846.
Townsend, A. et al. (1987) *Nature* 329: 482-483.
Turkewitz, A. P. et al. (1983) *Molec. Immunol.* 20: 1139-1147.
Unanue, E. R. et al. (1987) *Science* 236: 551-557.
Watts, T. H. et al. (1984) *Proc. Natl. Acad. Sci. USA* 81: 7564-7568.
Watts, T. H. et al. (1985) *Proc. Natl. Acad. Sci. USA* 82: 5480-5484.
Watts, T. H. et al. (1987) *Ann. Rev. Immunol.* 5: 461-475.
Clemetson, K. J. et al. (1986) In *Membrane proteins: A Laboratory Manual*, Ed. Azzi, A. et al., pp. 57-64.
Cooperman (1979) In *Ribosomes Structure, Function, and Genetics*. Ed. Chambliss et al. University Park Press, Baltimore Md. pp. 531-554.
Estess, P. et al. (1986) In *Regulation of immune gene expression*, Ed. Feldman, M. et al., Humana Press, pp. 3-19.
Guillet et al. (1987) *Science* 235: 865-870.
Hall et al. (1985) *Biochemistry* 24: 5702-5711.
Harcourt, G. et al. (1987) *Immunol. Today* 8 (11): (news and features section).
Hixson, J. R. *Medical Tribune* (Jan. 24, 1985) pp. 4-5.
Liu, M. A. et al. (1988) *Science* 239: 395-398.
Marrack, P. et al. (1988) *Nature* 332: 840-842.
Nakanishi, M. et al. (1983) *Molec. Immunol.* 20: 1227-1231.
Pastan, I. et al. (1986) *Cell* 47: 641-648.
Sekaly, R. P. et al. (1986) *J. Exp. Med.* 164: 1490-1504.
Shizuru, J. A. et al. (1988) *Science* 240: 659-662.
Springer, T. A. et al. (1976) *Proc. Natl. Acad. Sci. USA* 73: 2481-2485.
Sriram, S. et al. (1987) *Concepts Immunopathol.* 4: 275-286.
Vitetta, E. S. et al. (1987) *Science* 238: 1098-1104.
Watts, T. H. et al. (1988) In *Processing and presentation of antigens*, Academic Pres, pp. 143-154.
Margulies, D. H. et al. (1987) *Immunol. Res.* 6: 101-116.
Lamb et al. (1987) *EMBO J.* 6: 1245-1249.
Berkower et al. (1986) *J. Immunol.* 136: 2498-2502.
Townsend et al. (1986) *Cell* 44: 959-968.
Sanderson et al. (1973) *Transplantation* 16: 304-312.
Turner et al. (1976) *J. Biol. Chem.* 250: 4512-4519.
Gorga et al. (1987) *J. Biol. Chem.* 262: 16087-16094.
Zamvil et al. (1985) *J. Exp. Med.* 162: 2107-2124.
Zamvil et al. (1985) *Nature* 317: 355-358.
Ceredig, R. et al. (1986) *Eur. J. Immunol.* 16: 30-34.
Essery, G. et al. (1988) *Immunology* 64: 413-417.
Jenkins, M. K. et al. 91987) *J. Exp. Med.* 165: 302-319.
Klein, J. (1983) *Immunol. Reviews* 81: 177-202.
Lamb, J. R. (1983) *J. Exp. Med.* 157: 1434-1447.
Lamb, J. R. (1984) *Nature* 308: 72-74.
Lamb, J. R. et al. (1986) *Immunology* 57: 331-335.
Lamb, J. R. et al. (1987) *Eur. J. Immunol.* 17: 1641-1644.
Larche, M. et al. (1988) *Immunology* 64: 101-105.
Madsen, J. C. et al. (1988) *Nature* 332: 161-164.
Miller, S. D. et al. (1979) *J. Exp. Med.* 149: 758-773.
Nau, G. J. et al. (1987) *J. Immunol.* 139: 114-122.
Quill, H. et al. (1987) *J. Immunol.* 138: 3704-3712.
Suzuki, G. et al. (1988) *J. Immunol.* 140: 1359-1465.
Zanders, E. D. et al. (1983) *Nature* 303: 625-627.
Zanders, E. D. et al. (1985) *Eur. J. Immunol.* 15: 302-305.
Germain, R. N. (1981) *J. Immunol.* 127: 1964-1966.
Lamb, J. R. (1987) *EMBO J.* 6: 1245-1249.

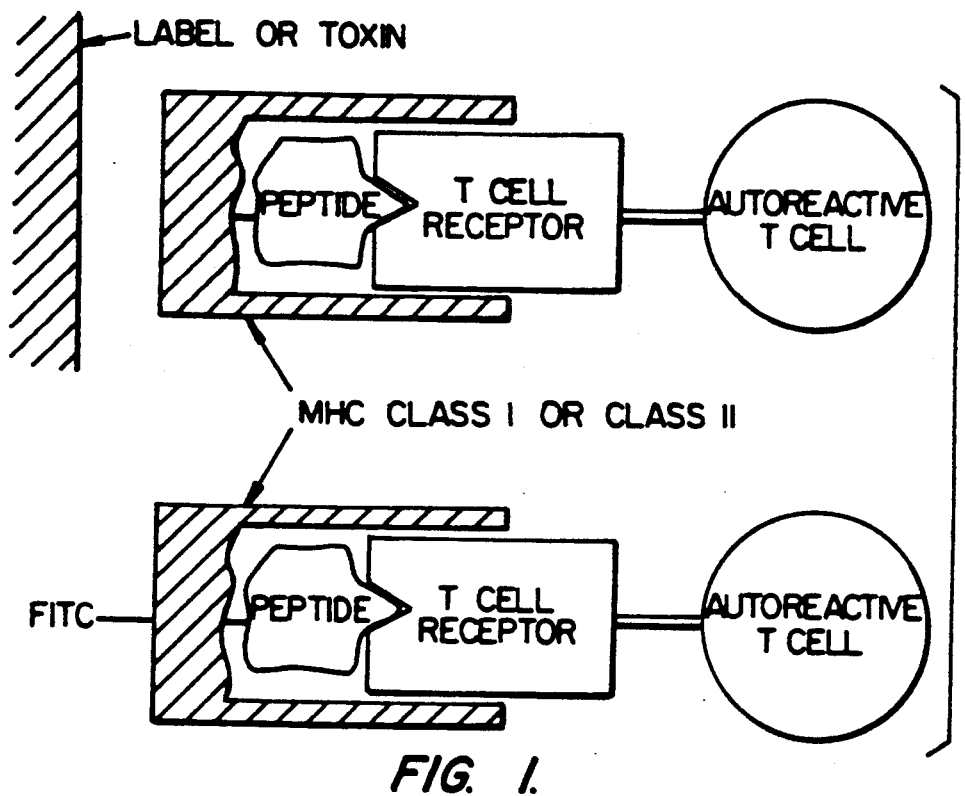
FIG. 1.
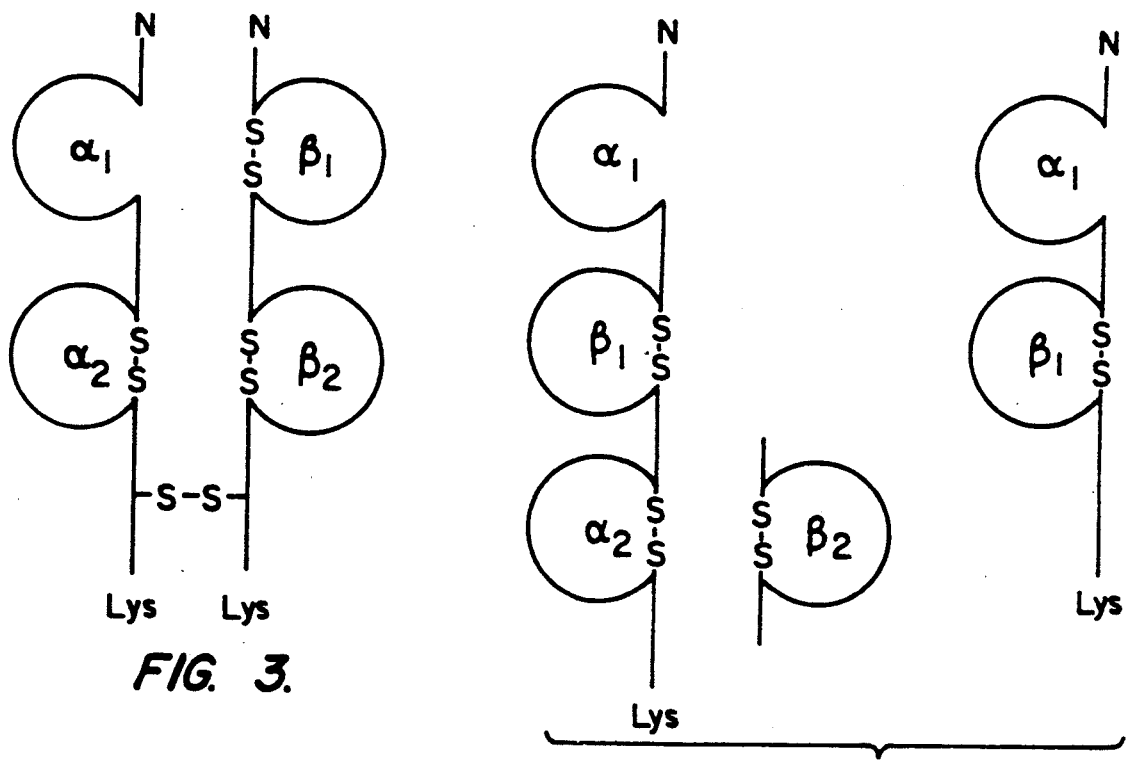
FIG. 3.
FIG. 4.

FIG. 6-1

```
Leu Leu Leu Phe Ser Cys Cys Gly Leu Val Leu Val Gly Ser Glu His Thr Arg
CUA CUG UUA UCG UGU UGU GGU CUG GUA CUA GGU UCU GAA CAU ACA CGU
         10          -20               -1  -1

Leu Val Ala Asn Leu Glu Asn Tyr Asn Lys Val Ile Arg Pro Val Glu His
UUG GUU GCU AAU UUA GAA AAU UAU AAC AAG GUG AUU CGU CCA GUG GAG CAU
 20              30           40            20            60

His Thr His Phe Val Asp Ile Thr Val Gly Leu Gln Ile Ile Leu Ile Ser
CAC ACC CAC UUU GUA GAU AUU ACA GUG GGG CUA CAG AUA CUC AUC AGU
     80              30               50              100         60

Val Asp Glu Val Asn Gln Ile Val Glu Thr Asn Val Arg Gln Gln Trp
GUG GAU GAA GUA AAU CAA AUU GUG GAA ACA AAU GUG CGC CAG CAA UGG
                    140                 70               160        180

Ile Asp Val Arg Leu Arg Trp Asn Pro Ala Asp Tyr Gly Gly Ile Lys Lys Ile
AUU GAU GUG AGG CUU CGC UGG AAU CCA GCC GAU UAU GGU GGA AUU AAA AAG AUC
                         200                              90              220

Arg Leu Pro Ser Asp Asp Val Trp Leu Pro Asp Leu Val Leu Tyr Asn Asn Ala
AGA CUG CCU UCU GAU GAU GUU UGG CUG CCA GAU UUA GUU CUG UAC AAC AAU GCU
     240                                  260                              280
```

```
                    100
Asp Gly Asp Phe Ala Ile Val His Met Thr Lys Leu Leu Asp Tyr Thr Gly
GAU GGU GAU UUU GCC AUU GUU CAC AUG ACC AAA CUG CUU GAU UAU ACG GGA
                    300                 320                     340
                                            110
Lys Ile Met Trp Thr Pro Pro Ala Ile Phe Lys Ser Tyr Gyx Glu Ile Ile Val
AAA AUA AUG UGG ACA CCU CCA GCA AUC UUC AAA AGC UAU UGU GAA AUU AUU GUA
                    360                     380                     130
                        120
Thr His Phe Asp Gln Gln Asn Cys Thr Met Lys Leu Gly Ile Trp Thr
ACA CAU UUC GAU CAA CAA AAU UGC ACU AUG AAG UUG GGA AUC UGG ACG
                    400                 420                     440      150
                        140                 160
Tyr Asp Gly Thr Lys Val Ser Ile Ser Pro Glu Ser Asp Arg Pro Asp Leu Ser
UAC GAU GGG ACA AAA GUU UCC AUA UCC CCG GAA AGU GAC CGU CCG GAU CUG AGU
                    460                     480                     500
                                            180
Thr Phe Met Glu Ser Gly Glu Trp Val Met Lys Asp Tyr Arg Gly Trp Lys His
ACA UUU AUG GAA AGU GGA GAG UGG GUA AUG AAA GAU UAU CGU GGA UGG AAG CAC
                    520                     540
            170                                         200
Trp Val Tyr Tyr Thr Cys Cys Pro Asp Thr Pro Tyr Leu Asp Ile Thr Tyr His
UGG GUG UAU UAU ACC UGC UGU CCU GAC ACU CCU UAC CUG GAU AUC ACC UAC CAU
                    560                     580                     600
                190

FIG. 6-2
```

```
                                    210                    220
Phe Ile Met Gln Arg Ile Pro Leu Tyr Phe Val Val Asn Val Ile Pro Cys
UUU AUC AUG CAG CGU AUU CCU CUU UAU UUU GUG AAU GUC AUC AUU CCU UGU
        620                 640                 660

Leu Leu Phe Ser Phe Leu Thr Gly Leu Val Phe Tyr Leu Pro Thr Asp Ser Gly
CUG CUU UUU UCA UUU UUA ACU GGA UUA GUA UUU UAC UUA CCA ACU GAU UCA GGU
        680                 700                             720

250
Glu Lys Met Thr Leu Ser Ile Ser Val Leu Leu Ser Leu Thr Val Phe Leu Leu
GAG AAG AUG ACU UUG AGU AUU UCC GUU CUG UUG ACU GUG UUC CUU CUG
        740                 760
                                270
Val Ile Val Glu Leu Ile Pro Ser Thr Ser Ser Ala Val Pro Leu Ile Gly Lys
GUU AUU GUU GAG CUG AUC CCC UCA ACU UCC AGC GCU GUG CCU UUG AUU GGC AAA
        780                 800                             820

280                                 290
Tyr Met Leu Phe Thr Met Ile Phe Val Phe Ser Ser Ile Ile Thr Val Val
UAC AUG CUU UUU ACA AUG AUU UUU GUC AUC AGU UCA AUC AUC ACU GUU GUU
        840                 860                             880

300                             310
Val Ile Asn Thr His Arg Ser Pro Ser Thr His Thr Met Pro Gln Trp Val
GUA AUU AAU ACU CAC CAU CGC UCU CCA AGU ACA CAU ACA AUG CCA CAA UGG GUA
        900                 920

FIG. 6-3
```

```
                                                       330
Arg Lys Ile Phe Ile Asp Thr Ile Pro Asn Val Met Phe Ser Thr Met Lys
CGA AAG AUC UUU AUU GAU ACU AUA CCC AAU GUU AUG UUU UCA ACA AUG AAA
940                         320                 980
                                             340
Arg Ala Ser Lys Glu Lys Gln Glu Asn Lys Ile Phe Ala Asp Asp Ile Asp Ile
CGA GCU UCU AAG GAA AAG CAA GAA AAU AAG AUA UUU GCU GAU GAC AUU GAU AUC
    1,000                        1,020                   1,040
              350                                    360
Ser Asp Ile Ser Gly Lys Gln Val Thr Gly Glu Val Ile Phe Gln Thr Pro Leu
UCU GAC AUU UCU GGA AAG CAA GUG ACA GGA GAA GUA AUU UUU CAA ACA CCU CUC
            1,060                        1,080
                370                                   380
Ile Lys Asn Pro Asp Val Lys Ser Ala Ile Glu Gly Val Lys Tyr Ile Ala Glu
AUU AAA AAU CCA GAU GUC AAA AGU GCU AUU GAG GGA GUC AAA UAU AUU GCA GAG
1,100                   1,120                        1,140
         390                                   400
His Met Lys Ser Asp Glu Ser Asn Ala Ala Glu Glu Trp Lys Tyr Val
CAC AUG AAG UCU GAU GAG UCA AAU GCU GCA GAG GAA UGG AAA UAU GUU
                    1,160                        1,180                1,200
                          410                                   420
Ala Met Val Ile Asp His Ile Leu Leu Cys Val Phe Met Leu Ile Cys Ile Ile
GCA AUG GUG AUU GAU CAC AUU CUG CUG UGU GUC UUC AUG CUG AUU UGU AUA AUU
                    1,220                   1,240                        1,260
                          430
Gly Thr Val Ser Val Phe Ala Gly Arg Leu Ile Glu Leu Ser Gln Gly Gly
GGU ACA GUU AGC GUG GCU GGC CGU CUC AUU GAA CUC AGU CAA GAG GGC UAA
                    1,280                        1,300

FIG. 6-4
```

His-Gly
N-Ac-Ala-Ser-Ala-Gln-Lys-Arg-Pro-Ser-Gln-Arg-Ser-Lys-Tyr-Leu-Ala-
(-)                                          10

Thr
Ser-Ala-Ser-Thr-Met-Asp-His-Ala-Arg-His-Gly-Phe-Leu-Pro-Arg-His-
                    20                                      30

Ile                    Gly
Arg-Asp-Thr-Gly-Ile-Leu-Asp-Ser-Leu-Gly-Arg-Phe-Phe-Gly-Ser-Asp-
                    40

Ser
Arg-Gly-Ala-Pro-Lys-Arg-Gly-Ser-Gly-Lys-Asp-Gly-His-His-Ala-Ala-Arg-
            50                                      60

Ala                                 Ser (-)        Thr
Thr-Thr-His-Tyr-Gly-Ser-Leu-Pro-Gln-Lys-Ala-Gln-Gly-His-Arg-Pro-Gln-
                    70                                      80

Me
Asp-Glu-Asn-Pro-Val-Val-His-Phe-Phe-Lys-Asn-Ile-Val-Thr-Pro-Arg-Thr-
                            90

Pro-Pro-Pro-Ser-Gln-Gly-Lys-Gly-Arg-Gly-Leu-Ser-Leu-Ser-Arg-Phe-Ser-
                100                                         110

Arg
Trp-Gly-Ala-Glu-Gly-Gln-Lys-Pro-Gly-Phe-Gly-Tyr-Gly-Gly-Arg-Ala-Ser-
                            120                                 130

Phe         Val
Asp-Tyr-Lys-Ser-Ala-His-Lys-Gly-Leu-Lys-Gly-His-Asp-Ala-Gln-Gly-Thr-
                                140

Leu-Ser-Lys-Ile-Phe-Lys-Leu-Gly-Gly-Arg-Asp-Ser-Arg-Ser-Gly-Ser-Pro-
            150                                             160

Met-Ala-Arg-Arg-COOH
            170

IAB ALPHA CHAIN

```
  1  AAT TCA TGC CGC GCA GCA GAG CTC TGA TTC TGG GGG TCC TCG CCC
     TTA AGT ACG GCG CGT CGT CTC GAG ACT AAG ACC CCC AGG AGC GGG

46  TGA CCA CCA TGC TCA GCC TCT GTG GAG GTG AAG ACG ACA TTG AGG
     ACT GGT GGT ACG AGT CGG AGA CAC CTC CAC TTC TGC TGT AAC TCC

91  CCG ACC ACG TAG GCA CCT ATG GTA TAA GTG TAT ATC AGT CTC CTG
     GGC TGG TGC ATC CGT GGA TAC CAT ATT CAC ATA TAG TCA GAG GAC

136  GAG ACA TTG GCC AGT ACA CAT TTG AAT TTG ATG GTG ATG AGT TGT
     CTC TGT AAC CGG TCA TGT GTA AAC TTA AAC TAC CAC TAC TCA ACA

181  TCT ATG TGG ACT TGG ATA AGA AGG AGA CTG TCT GGA TGC TTC CTG
     AGA TAC ACC TGA ACC TAT TCT TCC TCT GAC AGA CCT ACG AAG GAC

226  AGT TTG GCC AAT TGG CAA GCT TTG ACC CCC AAG GTG GAC TGC AAA
     TCA AAC CGG TTA ACC GTT CGA AAC TGG GGG TTC CAC CTG ACG TTT

271  ACA TAG CTG TAG TAA AAC ACA ACT TGG GAG TCT TGA CTA AGA GGT
     TGT ATC GAC ATC ATT TTG TGT TGA ACC CTC AGA ACT GAT TCT CCA

316  CAA ATT CCA CCC CAG CTA CCA ATG AGG CTC CTC AAG CGA CTG TGT
     GTT TAA GGT GGG GTC GAT GGT TAC TCC GAG GAG TTC GCT GAC ACA

361  TCC CCA AGT CCC CTG TGC TGG GTC AGC CCA ACA CCC TCA TCT
     AGG GGT TCA GGG GAC ACG ACC CAG TCG GGT TGT GGG AGT AGA
```

FIG 8-2

```
406 GCT TTG TGG ACA ACA TCT TCC CTC CTG TGA TCA ACA TCA CAT GGC
    CGA AAC ACC TGT TGT AGA AGG GAG GAC ACT AGT TGT AGT GTA CCG

451 TCA GAA ARA GCA AGT CAG TCG CAG ACG GTG TTT ATG AGA CCA GCT
    AGT CTT TYT CGT TCA GTC AGC ATC TGC CAC AAA TAC TCT GGT CGA

496 TCT TCG TCA ACC GTG ACT ATT CCT TCC ACA AGC TGT CTT ATC TCA
    AGA AGC AGT TGG CAC TGA TAA GGA AGG TGT TCG ACA GAA TAG AGT

541 CCT TCA TCC CTT CTG ACG ATG ACA TTT ATG ACT GCA AGG TGG AAC
    GGA AGT AGG GAA GAC TGC TAC TGT AAA TAC TGA CGT TCC ACC TTG

586 ACT GGG GCC TGG AGG AGC CGG TTC TGA AAC ACT GGG AAC CTG AGA
    TGA CCC CGG ACC TCC TCG GCC AAG ACT TTG TGA CCC TTG GAC TCT

631 TTC CAG CCC CCA TGT CAG AGC TGA CAG AGA CTG TGG TGT GTG CCC
    AAG GTC GGG GGT ACA GTC TCG ACT GTC TCT GAC ACC ACA CAC GGG

676 TGG GGT TGT CTG TGG GCC TTG TGG GCA TCG TGG TGG GCA CCA TCT
    ACC CCA ACA GAC ACC CGG AAC ACC AGC ACC ACC CGT GGT AGA

721 TCA TCA TTC AAG GCC TGC GAT CAG GTG GCA CCT CCA GAC ACC CAG
    AGT AGT AAG TTC CGG ACG CTA GTC CAC CGT GGA GGT CTG TGG GTC

766 GGC CTT TAT GA
    CCG GAA ATA CT
```

FIG. 9-1

IAB BETA CHAIN

```
  1  CAT TTC GTG TAC CAG TTC ATG GGC GAG TGC TAC TTC ACC AAC GGG
     GTA AAG CAC ATG GTC AAG TAC CCG CTC ACG ATG AAG TGG TTG CCC

46  ACG CAG CGC ATA CGA TAT GTG ACC AGA TAC ATC TAC AAC CGG GAG
     TGC GTC GCG TAT GCT ATA CAC TGG TCT ATG TAG ATG TTG GCC CTC

91  GAG TAC GTG CGC TAC GAC AGC GAC GTG GGC GAG CAC CGC GCG GTG
     CTC ATG CAC GCG ATG CTG TCG CTG CAC CCG CTC GTG GCG CGC CAC

136  ACC GAG CTG GGG CGG CCA GAC GCC GAG TAC TGG AAC AGC CAG CCG
     TGG CTC GAC CCC GCC GGT CTG CGG CTC ATG ACC TTG TCG GTC GGC

181  GAG ATC CTG GAG CGA ACG CGG GCC GAG CTG GAC ACG GTG TGC AGA
     CTC TAG GAC CTC GCT TGC GCC CGG CTC GAC CTG TGC CAC ACG TCT

226  CAC AAC TAC GAG GGG CCG GAG ACC CAC TCC CTG CGG CGG CTT
     GTG TTG ATG CTC CCC GGC CTC TGG GTG AGG GAC GCC GCC GAA

271  GAA CAG CCC AAT GTC GTC ATC TCC CTG TCC AGG ACA GAG GCC CTC
     CTT GTC GGG TTA CAG CAG TAG AGG GAC AGG TCC TGT CTC CGG GAG

316  AAC CAC CAC AAC ACT CTG GTC TGC TCA GTG ACA GAT TTC TAC CCA
     TTG GTG GTG TTG TGA GAC CAG AGT CAC TGT CTA AAG ATG GGT
```

FIG. 9-2

```
361  GCC AAG ATC AAA GTG CGC TGG TTC CGG AAT GGC CAG GAG GAG ACG
     CGG TTC TAG TTT CAC GCG ACC AAG GCC TTA CCG GTC CTC CTC TGC

406  GTG GGG GTC TCA TCC ACA CAG CTT ATT AGG AAT GGG GAC TGG ACC
     CAC CCC CAG AGT AGG TGT GTC GAA TAA TCC TTA CCC CTG ACC TGG

451  TTC CAG GTC CTG GTC ATG CTG GAG ATG ACC CCT CGG CGG GGA GAG
     AAG GTC CAG GAC TAC GAC CTC TAC TGG GGA GCC GCC CCT CTC

496  GTC TAC ACC TGT CAC GTG GAG CAT CCC AGC CTG AAG AGC CCC ATC
     CAG ATG TGG ACA GTG CAC CTC GTA GGG TCG GAC TTC TCG GGG TAG

541  ACT GTG GAG TGG AGG GCA CAG TCT GAG TCT GCC TGG AGC AAG ATG
     TGA CAC CTC ACC TCC CGT GTC AGA CTC AGA CGG ACC TCG TTC TAC

586  TTG AGC GGC ATC GGG GGC TGC GTG CTT GGG GTG ATC TTC CTC GGG
     AAC TCG CCG TAG CCC CCG ACG CAC GAA CCC CAC TAG AAG GAG CCC

631  CTT GGC CTT TTC ATC CGT CAC AGG AGT CAG AAA GGA CCT CGA GGC
     GAA CCG GAA AAG TAG GCA GTG TCC TCA GTC TTT CCT GGA GCT CCG

676  CCT CCT CCA GCA GGG CTC CTG CAG TGA
     GGA GGA GGT CGT CCC GAG GAC GTC ACT
```

| HPTYP # | FREQ %[2] | DQ | DQB1 | DQA1[3] | DRB1 | DRB3 | DRB4 | D | DISEASE ASSOCIATION[4] |
|---|---|---|---|---|---|---|---|---|---|
| 1. | 20 | w5(w1) | 1.1 | 1a | 1 | ne | ne | w1 | IDDM*, RA† |
| 2. |  | w5(w1) | 1.1 | 1a | 1 | ne | ne | w20 | IDDM |
| 3. | 26 | w6(w1) | 1.2 | 1b | w15(2) | ne | ne | w2 | CPMS, MG(T+) |
| 4. | 1.5 | w6(w1) | 1.12 | 1c | w15(2) | ne | ne | w12 |  |
| 5. | 1.5 | w5(w1) | 1.1 | ? | w16(2) | ne | ne | w21(AZH) | IDDM, MG(T-) |
| 6. | ? | w7(w3) | 3.1 | ? | w16(2) | ne | ne | w22 |  |
| 7. | 22 | w2 | ? | ? | w17(3) | 24(52) | ne | w3 |  |
| 8. |  | w2 | ? | ? | w17(3) | 25(52) | ne | w3 | DDM, MG(T-) |
| 9. | ? | w4(Wa) | Wa | ? | w18(3) | ?(52) | ne | ? |  |
| 10. | 9 | w8(w3) | 3.2 | 3 | 4 | ne | 53 | w4(4.2) | IDDM*, RA†, CPMS |
| 11. | 5 | w7(w3) | 3.1 | 3 | 4 | ne | 53 | w4(4.1) |  |
| 12. | 3 | w8(w3) | 3.2 | 3 | 4 | ne | 53 | w10 | IDDM*, CPMS |
| 13. | ? | w7(w3) | 3.1 | 3 | 4 | ne | 53 | w13 |  |
| 14. | 14 | w8(w3) | 3.2 | 3 | 4 | ne | 53 | w14 | IDDM*, RA†, CPMS |
| 15. | 0.5 | w4(Wa) | Wa | ? | 4 | ne | 53 | w15 | RA |

FIG. 10-1

| # | | | | | | | | | |
|---|---|---|---|---|---|---|---|---|---|
| 16. | 15 | {w7(w3) | 3.1 | 2 | w11(5) | 25(52) | ne | w5 | |
| 17. |    | {w7(w3) | 3.1 | 2 | w12(5) | 25(52) | ne | B6 | MG |
| 18. | 10 | {w5(w1) | 1.18 | 1c | w(13)(w6) | 24(52) | ne | w18 | |
| 19. | 3  | {w5(w1) | 1.18 | 1c | w(13)(w6) | 25(52) | ne | w18 | |
| 20. | 3  | w5(w1)  | 1.19 | 1b | w(13)(w6) | 26(52) | ne | w19 | |
| 21. | ?  | w6(w1)  | 1.9  | 1a | w(14)(w6) | 25(52) | ne | w9  | |
| 22. |    | w6(w1)  | 1.16 | 2  | w(14)(w6) | 24(52) | ne | w16 | |
| 23. | 1  | w9(w3)  | 3.3  | 3  | 7 | ne | 53 | w1  | |
| 24. | 27 | w2      | 2    | 3  | 7 | ne | 53 | w17 | |
| 25. | 6  | w4(Wa)  | Wa   | 1b | ne | w8/52 | ne | w8 | IDDM |
| 26. | 2  | ?(w3)   | ?    | 1b | ne | w8/52 | ne | w8 | |
| 27. | 1  | w9(w3)  | 3.3  | 3  | 9  | ne | 53 | w23 | RA |
| 28. | ?  | w5(w1)  | 1.1  | 1a | w10 | ? | ? | ? | |

FIG. 10-2

100 C3H/HeN MICE, 8-9 WEEKS OLD        $CH_{27}$ CELLS = $1 \times 10^{10}$
TOTAL SPLEEN CELLS = $4.5-6.0 \times 10^9$ CULTURED FOR 36 HOURS AT $3 \times 10^6$ CELLS/ml
WITH 100 μg/ml LPS AND 5% FCS LYSED CELLS AND HOMOGENIZED IN
10mM TRIS HCl pH 8.3, 1mM PMSF .02% $NaN_3$
(FOR $5 \times 10^9$ CELLS, 50ml BUFFER WAS USED)

CENTRIFUGED FOR 15 MIN. AT
2,000 × g AT 4°C
PELLET / TO REMOVE CELL DEBRIES
SUPERNATANT

CENTRIFUGED FOR 60 MIN. AT
SUPERNATANT / 100,000 × g AT 4°C
PELLET

SUSPENDED IN DNase I BUFFER
(10mM TRIS HCl pH 8.3, 1mM EDTA, 0.5mg/ml DNase I)
FOR $5 \times 10^9$ CELLS, 10ml BUFFER WAS USED

25°C FOR 1 HOUR WITH GENTLE
CONSTANT SHAKING

ADDED HIGH SALT/EDTA BUFFER
(10mM TRIS pH 8.3, 0.5 M NaCl, 5mM EDTA,
1mM PMSF AND .02% $NaN_3$)
FOR $5 \times 10^9$ CELLS, 50 ml BUFFER WAS USED 4°C FOR 30 MIN. WITH GENTLE
SHAKING CENTRIFUGED FOR 60
SUPERNATANT / MIN. AT 100,000 × g AT 4°C
PELLET SUSPENDED IN NP-40 BUFFER
(10mM TRIS HCl pH 8.3, 0.5% NP40,
0.1 M NaCl, 5mM EDTA, 0.02% $NaN_3$ AND 1mM PMSF)
FOR $5 \times 10^9$ CELLS, 50 ml BUFFER WAS USED CENTRIFUGE FOR 60 MIN. AT
PELLET / 100,000 × g AT 4°C SUPERNATANT
(TOTAL PROTEIN = 18-23 mg)

FIG. 12.

10-2.16 Mab WERE PURIFIED ON PROTEIN-A COLUMN FROM 5 ml ASCITES, 30mg PURE Ab WERE RECOVERED. A STANDARD PROCEDURE (MAPS II) FROM Bio-Rad LABORATORIES WAS FOLLOWED

COUPLED TO CNBr ACTIVATED SEPHAROSE 4B (3-4 mg Ab/ml OF WET GEL) STANDARD PROCEDURE FROM PHARMACIA WAS FOLLOWED EXTENT OF COUPLING → 98%

PURIFIED IgG WAS ANALYZED ON 10% ID POLYACRYLAMIDE GEL FOLLOWED BY COOMASSIE BRILLIANT BLUE R-250

*FIG. 13a.*

ONE DIMENSIONAL POLYACRYLAMIDE
GEL ANALYSIS OF PURIFIED 10-2.16
MONOCLONAL ANTIBODY

ONE DIMENSIONAL POLYACRLAMIDE
GEL ANALYSIS OF IAk

WASHED 10-2.16 ANTIBODY COLUMN WITH LOW AND HIGH pH
BUFFERS AND EQUILIBRATED WITH 0.5% NP-40 BUFFER, pH
8.3 (10mM TRIS HCl pH 8.3, 0.5% NP40, 0.1 M NaCl,
5 mM EDTA, 0.02% NaN$_3$ AND 1mM PMSF)

APPLIED 50ml MEMBRANE FRACTION (20-25mg TOTAL PROTEIN)
TO A 4ml BED VOLUME COLUMN CONTAINING 15-20mg
COUPLED ANTIBODIES (CIRCULATED OVERNIGHT AT 4°C)

WASHED COLUMN WITH 10 BED VOLUMES OF
0.5% DOC BUFFER, pH 8.3
(1mM TRIS HCl, pH 8.3, 0.5% DEOXYCHOLATE, 0.1 M NaCl,
5mM EDTA, 0.02% NaN$_3$ AND 5mM PMSF)

WASHED WITH 5 BED VOLUMES OF
1% OG BUFFER IN PHOSPHATE BUFFER, pH 8.3
(20mM PHOSPHATE pH 8.3, 0.1 M NaCl, 1% OCTYLGLUCOSIDE
.02% NaN$_3$ AND 5mM PMSF)

ELUTED WITH 1% OG IN PHOSPHATE BUFFER, pH 11.0
(20mM PHOSPHATE pH 11, 0.1 M NaCl, 1% OCTYLGLUCOSIDE
.02% NaN$_3$ AND 5 mM PMSF)
NEUTRALIZED EACH 1ml FRACTION WITH 12 μl OF 1 M ACETIC ACID

POOLED PEAK WAS CONCENTRATED (5-10 FOLD)
BY VACUUM DIALYSIS

TOTAL 1-A$^k$ = 200-300 μg (FROM 5X10$^9$ SPLEEN CELLS)
ANALYZED ON 10% PAGE FOLLOWED BY SILVERSTAIN

*FIG. 14.*

MHC-MEDIATED TOXIC CONJUGATES USEFUL IN AMELIORATING AUTOIMMUNITY

CROSS-REFERENCE TO RELATED APPLICATIONS

This application is a continuation-in-part of applicants' copending U.S. patent application Ser. No. 07/576,084, filed Aug. 30, 1990, now U.S. Pat. No. 5,130,297, which is a continuation of U.S. patent application Ser. No. 07/210,594, filed Jun. 23, 1988, now abandoned, and a continuation-in-part of U.S. patent application Ser. No. 07/367,751 filed Jun. 21, 1989, now U.S. Pat. No. 5,194,425, all of which are, in their entirety, incorporated herein by reference.

TECHNICAL FIELD

The invention relates to the treatment of autoimmune diseases and to materials and methods useful in therapy and diagnosis of such diseases. In particular, it concerns complexes which target helper T-cells by using a complex of the major histocompatibility complex (MHC) glycoproteins with peptides representing fragments of antigens associated with autoimmunity. These complexes can be further conjugated to radioisotopes or other labels for diagnostic purposes, or to toxins or other substances which render the complexes therapeutically useful.

BACKGROUND OF THE INVENTION

More than 30 autoimmune diseases are presently known; these include many which have received much public attention, including myasthenia gravis (MG) and multiple sclerosis (MS). Characteristic of these disease is the attack by the immune system on the tissues of the victim—these tissue antigens being resistant in non-diseased individuals because of their recognition by the immune system as "self." In autoimmune diseases, this recognition apparently does not occur, and the tissue of the afflicted subject is treated as an invader—i.e., the immune system sets about destroying this presumed foreign target.

A crude approach to treating autoimmune disease is, of course, general immunosuppression. This has the obvious disadvantage of crippling the ability of the subject to respond to real foreign materials to which it needs to mount an immune response. An only slightly more sophisticated approach relies on the removal of antibodies or immune complexes involving the target tissue. This also has adverse side effects, and is difficult to accomplish. The invention approach, described in detail below, relies on a "clonotypic" reagent—i.e., a reagent which attacks only the cells of the immune system which are responsive to the autoantigen.

In the general paradigm now considered to describe the immune response, specific antigens presented result in a clonal expansion, as first proposed by Burnet in 1959. According to this scenario, a particular subject will have hundreds of thousands of T and B cells each bearing receptors that bind to different antigenic determinants. Upon exposure to an antigen, the antigen selectively binds to cells bearing the appropriate receptors for the antigenic determinants it contains, ignoring the others. The binding results in a cloned population of thousands of daughter cells, each of which is marked by the same receptor. A clonotypic reagent affects only a subset of the T and B cells which are appropriate for the antigen of interest. In the case of the invention compositions, the antigenic determinant is usually that associated with an autoimmune disease.

The clonotypic reagent compositions of the invention are specifically designed to target T-helper cells which represent the clones specific for the antigenic determinant(s) of the tissue which is affected by the autoimmune disease. T-helper cells recognize a determinant only in association with an MHC protein; the complexes of the invention therefore include an effective portion of the MHC protein.

There have, recently, been some related approaches which attempt to interdict the immune response to specific antigens. For example, the autoantigen thyroglobulin has been conjugated to ricin A and the conjugate was shown to suppress specifically the in vitro antibody response of lymphocytes which normally respond to this antigen. It was suggested that such immunotoxins would specifically delete autoantibody-secreting lymphocyte clones (Rennie, D. P., et al., Lancet (Dec. 10, 1983) 1338–1339). Diener, E., et. al , Science (1986) 231:148–150 suggested the construction of compounds which cause antigen-specific suppression of lymphocyte function by conjugating daunomycin to the hapten (in this case, of ovalbumin) using an acid-sensitive spacer. The conjugate caused hapten-specific inhibition of antibody secretion by B lymphocytes in vitro and in vivo. A conjugate of daunomycin (with an acid-sensitive spacer) to a monoclonal antibody-specific to T-cells also eliminated the response by T-lymphocytes to concanavalin A. Steerz, R. K. M., et al., J. Immunol. (1985) 134:841–846 utilized radiation as the toxic element in a toxin conjugate. Rats were administered a radioactively labeled, purified receptor from electric fish, prior to injection with cold receptor. Injection with this receptor is a standard procedure to induce experimental autoimmune myasthenia gravis (EAMG). Control rats that received preinjection only either of cold receptor or radiolabeled albumin, prior to administration of receptor to induce the disease develop the symptoms of EAMG; those pretreated with radioactively-labeled receptor showed reduced symptoms. It was surmised that the labeled, and therefore destructive, receptor selectively eliminated immunocompetent cells. Similar work utilizing a ricin/receptor conjugate for pretreatment was reported by Killen, J. A., et al., J. Immunol. (1984) 133:2549–2553.

A less specific approach which results in the destruction of T-cells in general is treatment with an IL-2/toxin conjugate as reported by Hixson, J. R., Medical Tribune (Jan. 28, 1988) 4–5. In a converse, but related, approach Liu, M. A., et al., Science (1988) 239:395–397, report a method to "link up" cytotoxic T-cells with a desired target regardless of the cytotoxic T-cell specificity. In this approach, antibody specific to the universal cytotoxic T-lymphocytes to destroy human melanoma cells when melanocyte-stimulating hormone was the hormone used.

The current model of immunity postulates that antigens mobilize an immune response, at least in part, by being ingested by an antigen-presenting cell (APC) which contains on its surface a Class II glycoprotein encoded by a gene in the major histocompatibility complex (MHC). The antigen is then presented to a specific T helper cell in the context of the surface bound MHC glycoprotein, and by interaction of the antigen specific T cell receptor with the antigen—MHC complex, the T helper cell is stimulated to mediate the antigen-specific immune response, including induction of cytotoxic T-cell function, induction of B cell function, and secretion of a number of factors aiding and abetting this response.

The involvement of the MHC Class II proteins in autoimmune disease has been shown in animal models. Administration of antibodies to either MHC Class II proteins themselves or antibodies to agents that induce expression of the MHC Class II genes interferes with development of the autoimmune condition in these model systems. The role of helper T-cells has also been demonstrated in these models by counteracting the autoimmune system using anti-CD4 monoclonal antibodies; CD4 is the characteristic helper T-cell receptor (Shizuru, J. A. et al., *Science* (1988) 240:659–662).

SUMMARY OF THE INVENTION

The invention is directed to methods to identify and destroy those aspects of the immune system which are responsible for undesirable autoimmunity. The invention composition and methods are designed to target helper T-cells which recognize a particular antigen in association with a glycoprotein encoded by the MHC. The invention complexes effectively substitute for the antigen-presenting cell in evoking the interaction of the T-lymphocytes and other cells of the immune system with respect to antigen. It has been shown that isolated MHC Class II antigen in and of itself can effectively replace the antigen-presenting cell in the presentation of antigen epitopes to a T-helper lymphocyte (Watts, T. H., et al., *Proc. Natl. Acad. Sci. USA* (1984) 81:7564–7568) which is incorporated herein by reference. However, by substituting an effector function, such as a toxin, for the antigen presenting cell (APC) surface, the antigen is made effective in destroying the immune response it would otherwise create. By substituting a label for the APC surface, the antigen is used to identify the portions of the immune system with which it interacts.

The invention provides forms of an autoantigen which interact with the immune system, in a manner analogous to those initiated by the autoantigen itself to cause the autoimmune reaction, but with modifications to provide additional functions, for example, those which permit identification of the relevant portions of the immune system, and, others which destroy the capacity of the immune system to respond in this undesirable manner.

In one embodiment, the invention compositions are three component complexes of (1) an effective portion of the MHC-encoded antigen-presenting glycoprotein; (2) an effective portion of the antigen; and (3) an effector. The first two components, which may be bound covalently or by noncovalent association, are in turn conjugated to the third, effector, component, most commonly a toxin or a label. The effector component, substitutes for the APC surface, and alters the effect of the complex with regard to the immune system target.

In another embodiment, the invention compositions are purified two component complexes of (1) an effective portion of the MHC-encoded antigen-presenting glycoprotein; and (2) an effective portion of the antigen. These two components may be bound covalently or by noncovalent association.

Thus, in one aspect, the invention is directed to compositions of matter which are the above-described complexes. Each component of the complex is associated with, or coupled to, another component by, for example, noncovalent association or covalent bonding. In other aspects, the invention is directed to pharmaceutical compositions wherein the complexes of the invention are active ingredients, to methods of down-regulating the immune system with regard to a particular antigen, specifically a self-antigen, and to methods to identify portions of the immune system reactive with a specific antigen, using the complexes and pharmaceutical compositions of the invention.

Accordingly, one aspect of the invention is a complex of the formula $$X \overset{1}{-} MHC \overset{2}{-} peptide \quad (1),$$

or $$MHC \overset{2}{-} peptide \overset{1}{-} X \quad (2);$$

wherein X represents a functional moiety selected from a toxin and a labeling group;

MHC is an effective portion of the MHC glycoprotein, said glycoprotein dissociated from the cell surface on which it normally resides;

"peptide" represents an epitope-containing antigenic peptide associated with an autoantigen;

$\overset{1}{-}$ represents a covalent bond or a bivalent linker bound to X and MHC in Formula (1) or to X and peptide in Formula (2) by covalent bonds; and $\overset{2}{-}$ represents a covalent bond, a noncovalent association, or a linker covalently bound to, or associated with the MHC and peptide.

Another aspect of the invention is a method to treat an autoimmune disease in a vertebrate subject which method comprises administering to a vertebrate in need of such treatment the complex or a pharmaceutical composition in which the complex is the active ingredient, wherein X is a toxin.

Yet another aspect of the invention is a method to monitor an autoimmune disease in a vertebrate subject which method comprises administering to a vertebrate in need of such treatment the complex or a pharmaceutical composition in which the complex is the active ingredient, wherein X is a label.

Still another aspect of the invention is a method to prepare a composition of the formula $$MHC \overset{1}{-} peptide,$$

wherein MHC, $\overset{2}{-}$, and peptide are defined as in claim 1;

which method comprises isolating the MHC-II glycoprotein from MHC-II containing cells;

incubating said MHC with the peptide; and removing the excess peptide by dialysis.

BRIEF DESCRIPTION OF THE DRAWINGS

FIG. 1 is a diagram of a typical complex of the invention.

FIG. 2 shows the 3-dimensional structure of the human HLA-A2 antigen (Class I).

FIG. 3 shows a diagrammatic representation of the active portion of a modified Class II MHC-encoded glycoprotein.

FIG. 4 shows preferred second generation MHC protein designs.

FIG. 5 is a diagram of a planar membrane bilayer including the MHC glycoprotein, mimicking the surface of the antigen presenting cell.

FIG. 6 shows the amino acid sequence and encoding mRNA for the alpha subunit of acetylcholine receptor protein.

FIG. 7 shows the amino acid sequence of myelin basic protein.

FIG. 8 shows the nucleotide sequence encoding the I-A$^b$-alpha chain.

FIG. 9 shows the nucleotide sequence encoding the I-A$^b$-beta chain.

FIG. 10 presents a list of the DQ/DR haplotypes in humans and their associations with autoimmune diseases.

Figure 11:
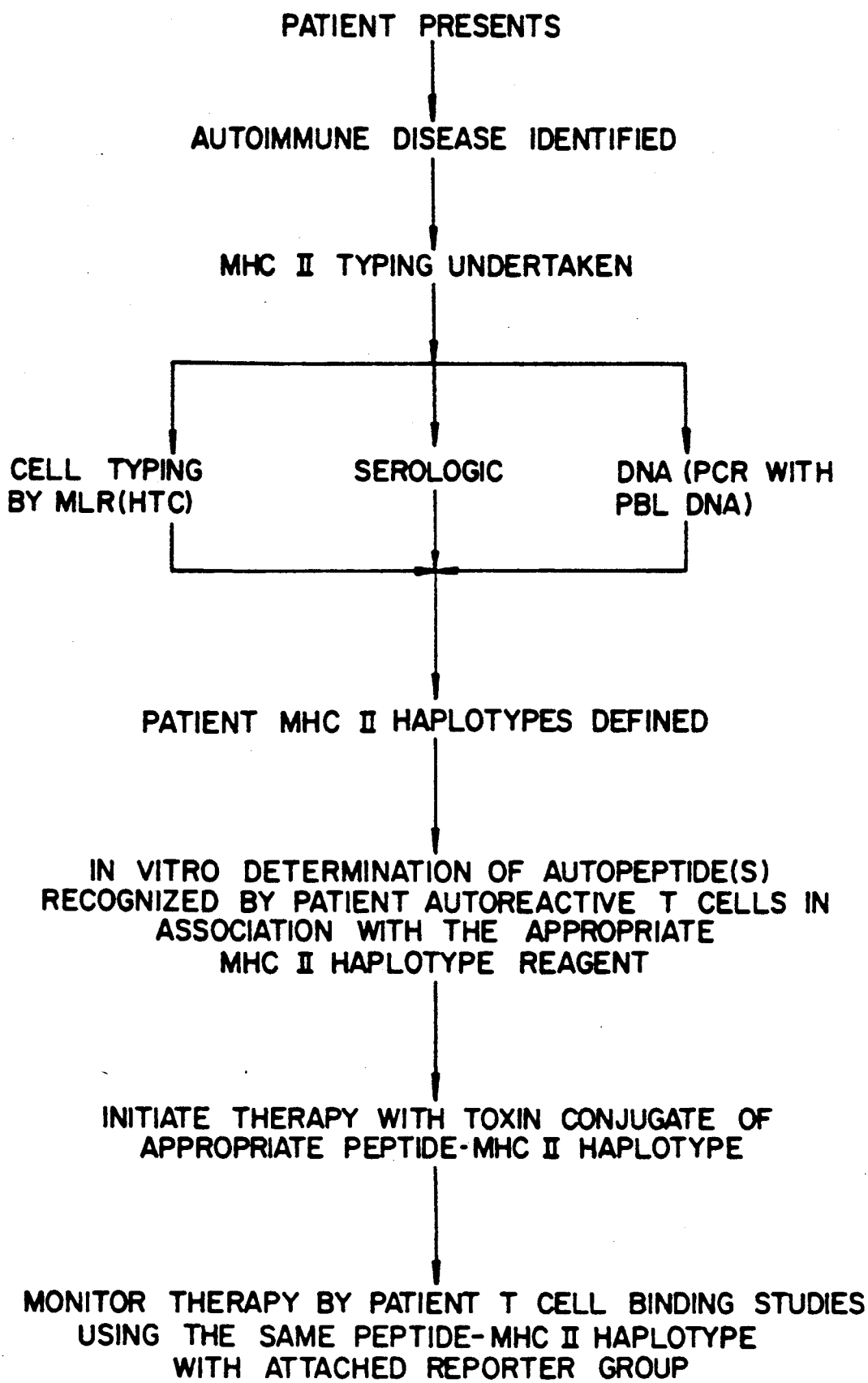

FIG. 11 shows a protocol suitable for the utilization of the complexes of the invention for the diagnosis and/or treatment of an autoimmune disease.

FIG. 12 shows a scheme for the preparation of I-A$^k$ containing NP-40 soluble membrane extracts.

FIG. 13A is a scheme for the affinity purification of 10-2.16 monoclonal antibody and its coupling to CNBr activated Sepharose 4B.

Figure 13B:
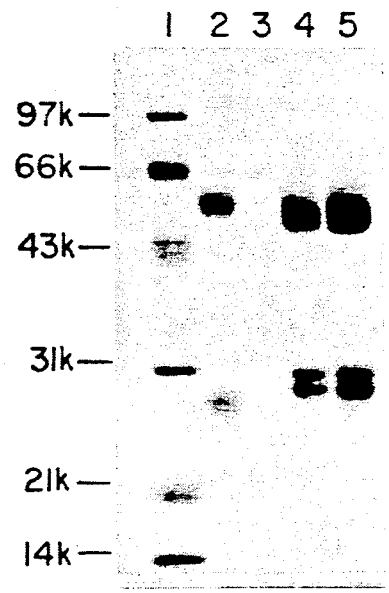

FIG. 13B is a copy of a gel showing the purity of 10-2.16 monoclonal antibody purified by the scheme in FIG. 13A.

FIG. 14 shows a scheme for the purification of I-A$^k$.

Figure 15:
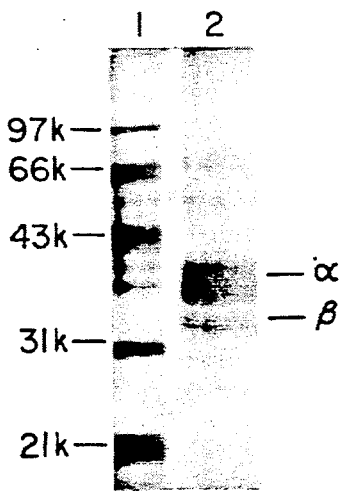

FIG. 15 is a polyacrylamide gel showing the purity of I-A$^k$ purified by the scheme in FIG. 14.

Figure 16:
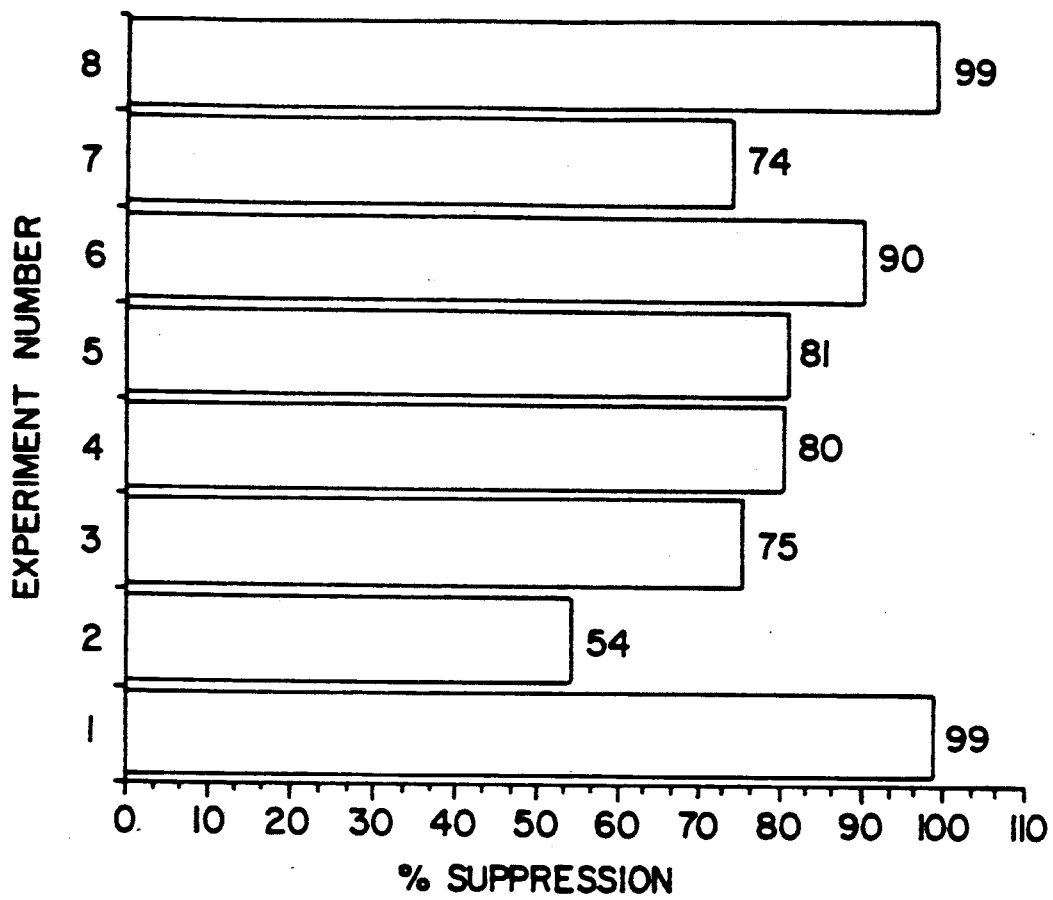

FIG. 16 is a bar graph showing the results of eight studies on the inhibition of proliferation by a complex containing I-A$^k$ and MBP (1-13); I-A$^k$ is also called IA$^k$.

Figure 17:
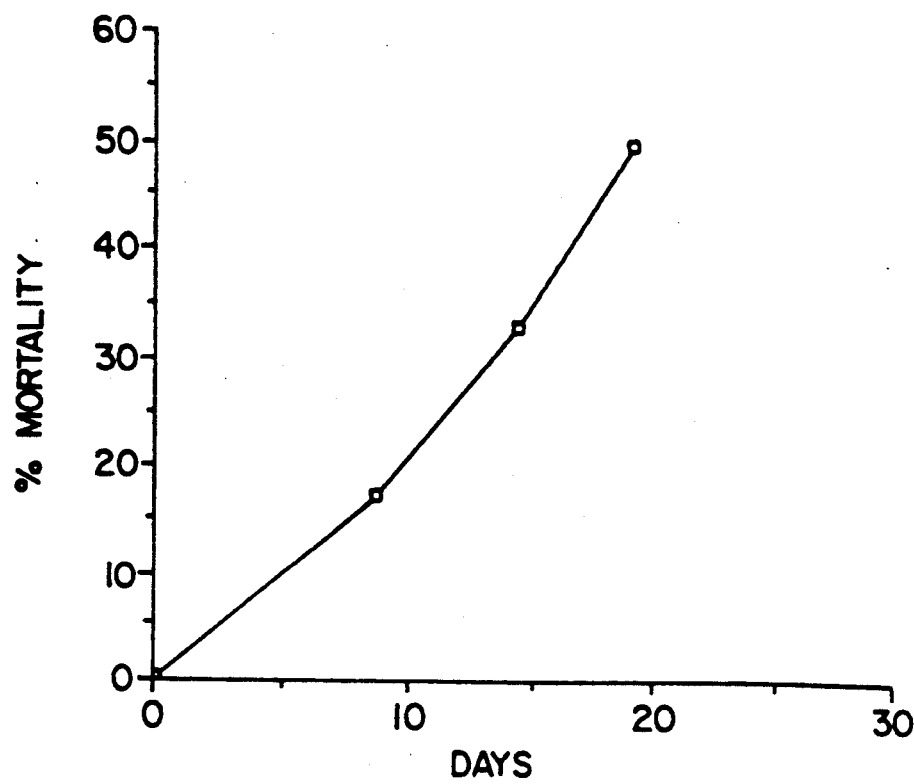

FIG. 17 is a graph showing the development of EAE in mice resulting from immunization with MBP (1-13).

Figure 18:
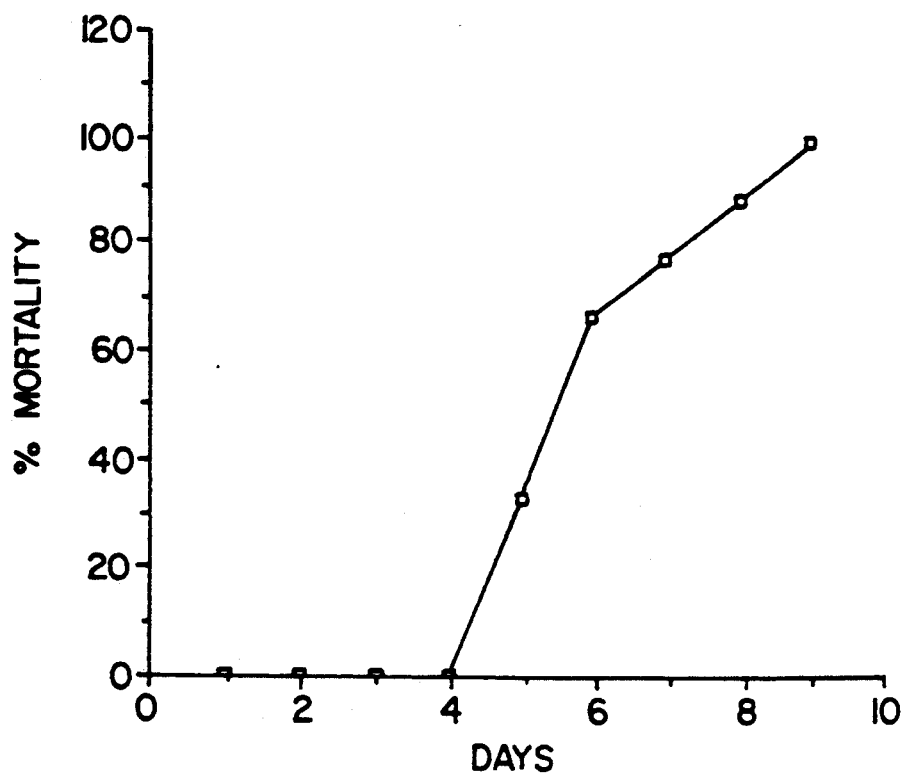

FIG. 18 is a graph showing the adoptive transfer of EAE by T cell clone 4R3.4, obtained from B10A(4R) strain of mice following immunization with MBP(1-11).

Figure 19:
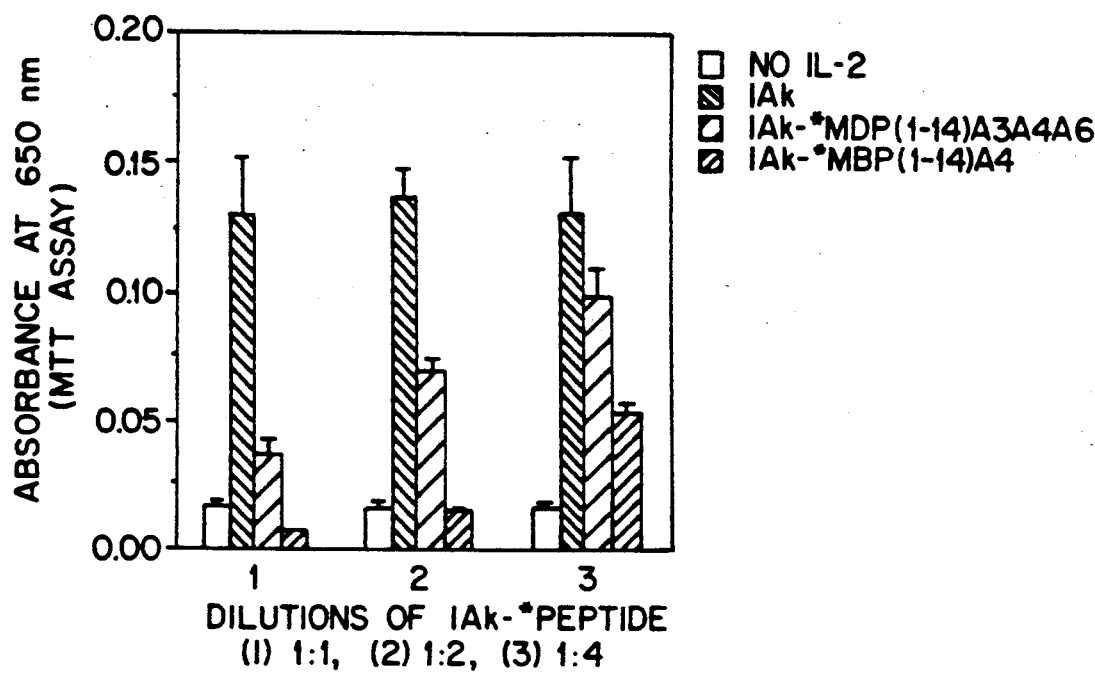

FIG. 19 is a bar graph showing lethal irradiation of AJ1.2 T cells with a complex containing I-A$^k$ and $^{131}$I radiolabeled MBP(1-14). The open bar represents proliferation of cells grown in the absence of interleukin-2 (IL-2). The solid bar represents proliferation of cells grown in the presence of unlabelled I-A$^k$. The bar with light cross-hatching represents cells grown in the presence of a complex comprising a radiolabeled peptide not recognized by AJ1.2 cells. The bar with heavy cross hatching represents cells grown in the presence of a complex comprising a radiolabeled peptide recognized by AJ1.2 cells.

Figure 20A:
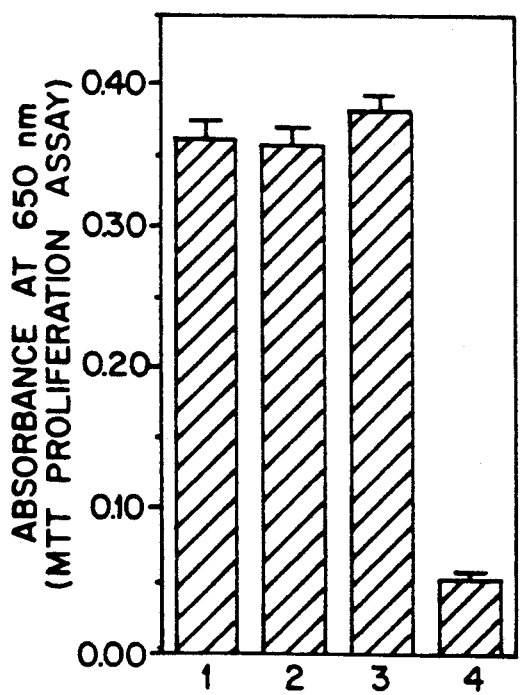
Figure 20B:
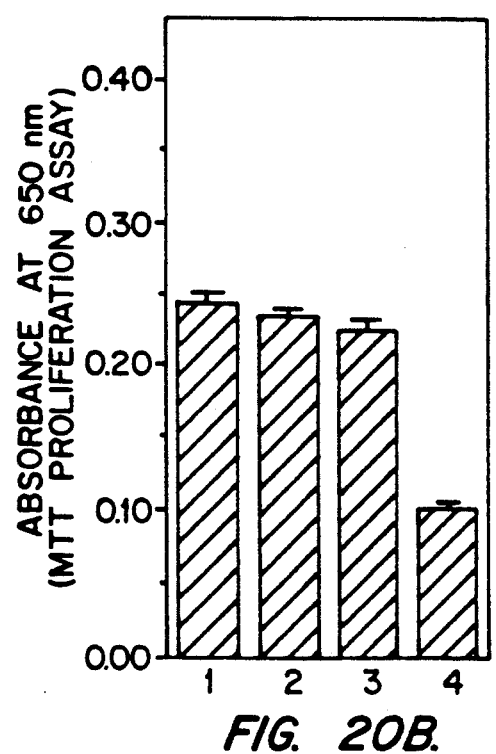

FIG. 20a is a bar graph showing elimination of AJ1.2 T cells using a complex containing I-A$^k$ and MBP(1-14-)A4 peptide conjugated to adriamycin. FIG. 20b shows the results of the same experiment using 4R3.9 T cells. In each figure, No. 1 represents proliferation of cells alone, No. 2 represents proliferation of cells incubated with unconjugated complexes, No. 3 represents proliferation of cells incubated with complexes comprising ovalbumin peptide conjugated to adriamycin, and No. 4 represents cells incubated with complexes comprising MBP(1-14)A4 conjugated to adriamycin.

Figure 21:
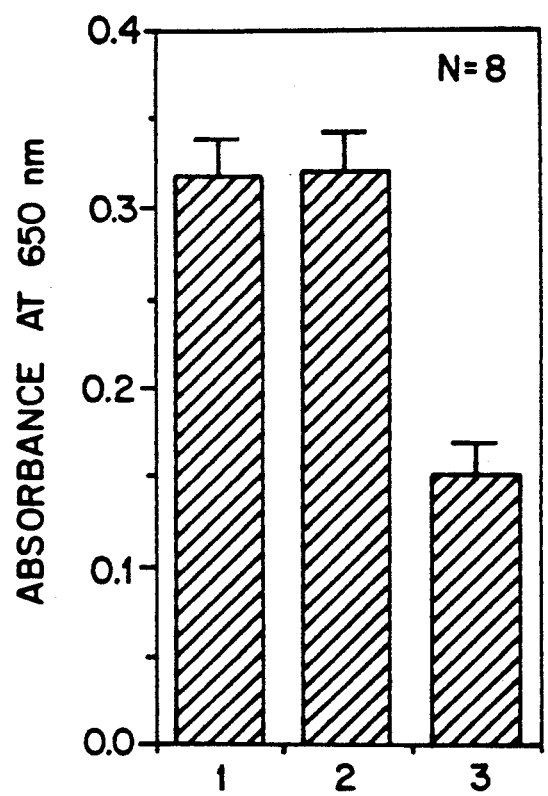

FIG. 21 is a bar graph showing elimination of AJ1.2 T cells using a complex containing I-A$^k$ and MBP(1-14-)A4 peptide conjugated to mycophenolate. No. 1 represents proliferation cells alone, No. 2 represents proliferation of cells incubated with unconjugated complexes and No. 3 represents proliferation of cells incubated with complexes comprising MBP(1-14)A4 peptide conjugated to mycophenolate.

DESCRIPTION OF PREFERRED EMBODIMENTS

The invention complexes contain at least two components: a peptide which represents an autoantigen or other antigenic sequence with the relevant effect on the immune system and an effective portion of the MHC-encoded glycoprotein involved in antigen presentation. An effective portion of an MHC glycoprotein is one which comprises the antigen binding pocket and sequences necessary for recognition of the MHC-peptide complex by the appropriate T cell receptor. A third component, an effector component which is generally a toxin or a label may also be included. In general, the effector portion is covalently conjugated to the MHC-encoded glycoprotein or, in some cases, to the autoantigenic peptide; the association between the peptide antigen and the antigen binding pocket of the MHC protein can be by covalent or by noncovalent bonding. Each of the components of the system is described separately below; followed by description of the methods by which these complexes can be prepared, evaluated and employed.

THE MHC-DERIVED COMPONENT

The glycoproteins encoded by the MHC have been extensively studied in both the human and murine systems. In general, they have been classified as Class I glycoproteins, found on the surfaces of all cells and primarily recognized by cytotoxic T-cells; and Class II which are found on the surfaces of several cells, including accessory cells such as macrophages, and are involved in presentation of antigens to helper T-cells. Some of the histocompatibility proteins have been isolated and characterized. The term "isolated MHC component" as used herein refers to an MHC glycoprotein or an effective portion of an MHC glycoprotein (i.e., one comprising an antigen binding pocket and sequences necessary for recognition by the appropriate T cell receptor) which is in other than its native state, for example, not associated with the cell membrane of a cell that normally expresses MHC. As described in detail below, the MHC component may be recombinantly produced, solubilized from the appropriate or associated with a liposome.

Methods for purifying the murine I-A (Class II) histocompatibility proteins have been disclosed by Turkewitz, A. P., et al., *Molecular Immunology* (1983) 20:1139–1147, which is incorporated herein by reference. The isolated antigens encoded by the I-A and I-E subregions were shown to consist of two noncovalently bonded peptide chains: an alpha chain of 32–38 kd and a beta chain of 26–29 kd. A third, invariant, 31 kd peptide is noncovalently associated with these two peptides, but it is not polymorphic and does not appear to be a component of the antigens on the cell surface (Sekaly, R. P., *J. Exp. Med.* (1986) 164:1490–1504, which is incorporated herein by reference). The alpha and beta chains of seven allelic variants of the I-A region have been cloned and sequenced (Estees, "T-cell Clones", 3-19).

The human Class I proteins have also been studied. The MHC of humans (HLA) on chromosome 6 has three loci, HLA-, HLA-B, and HLA-C, the first two of which have a large number of alleles encoding alloantigens. These are found to consist of a 44 kd subunit and a 12 kd beta$_2$-microglobulin subunit which is common to all antigenic specificities. Isolation of these detergent-soluble HLA antigens was described by Springer, T. A., et al., *Proc. Natl. Acad. Sci. USA* (1976) 73:2481–2485; Clementson, K. J., et al., in "Membrane Proteins" Azzi, A., ed; Bjorkman, P., Ph.D. Thesis Harvard (1984) all of which are incorporated herein by reference.

Figure 2A:
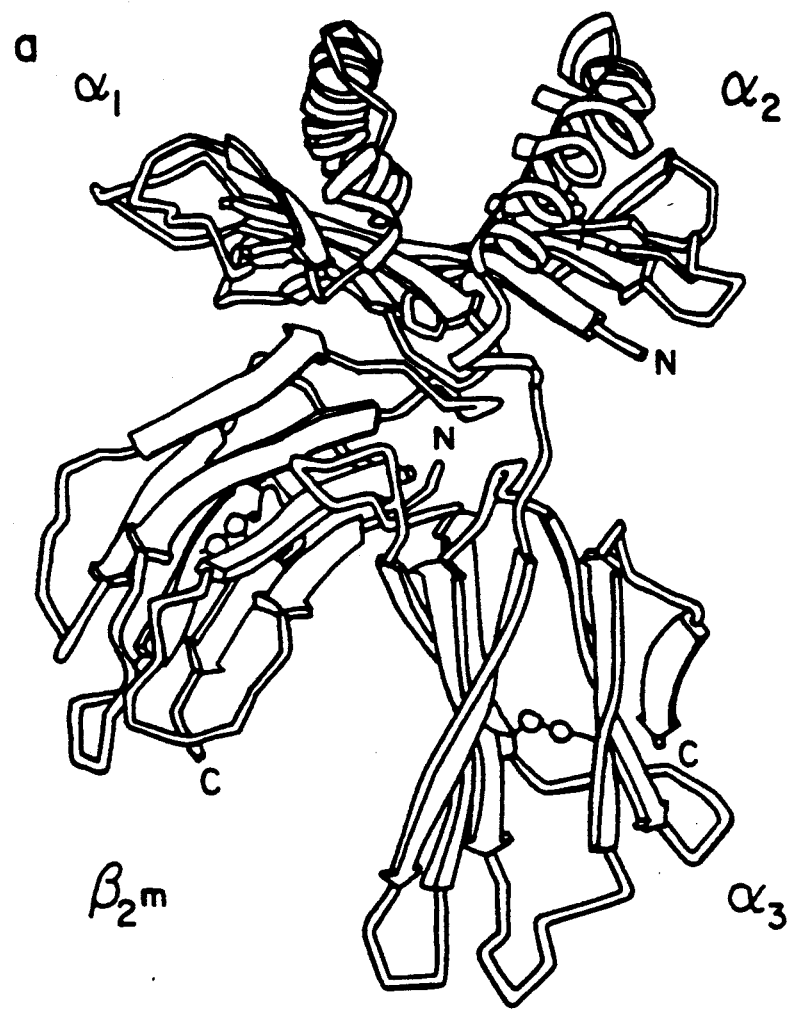
Figure 2B:
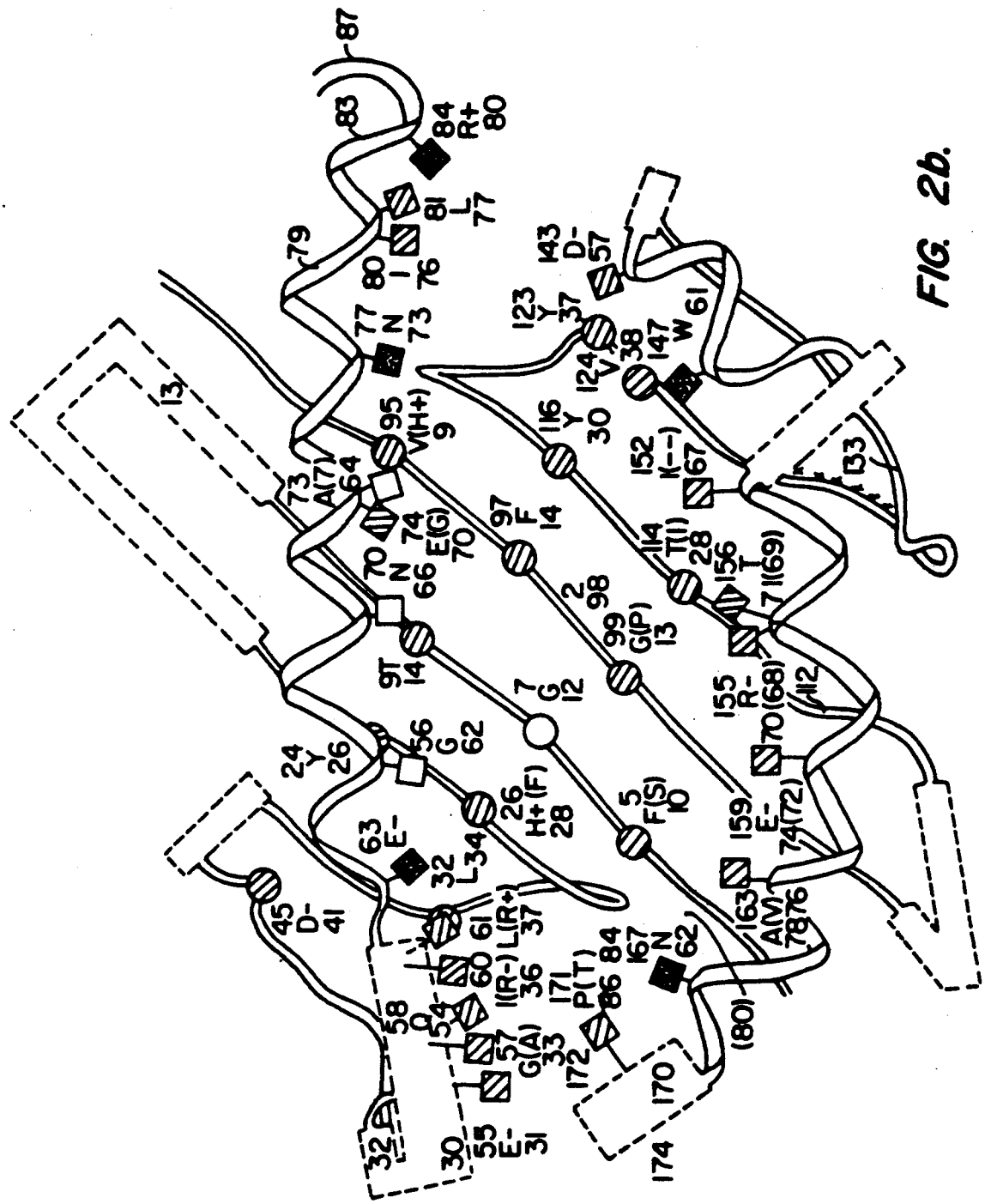

Further work has resulted in a detailed picture of the 3-D structure of HLA-A2, a Class I human antigen. (Bjorkman, P. J., et al., *Nature* (1987) 329:506–512, 512–518 which is incorporated herein by reference). In this picture, the beta2-microglobulin protein and alpha$_3$ segment of the heavy chain are associated; the alpha$_1$ and alpha$_2$ regions of the heavy chain appear to form the base of the antigen-binding pocket to which the peptide is bound (Science (1987) 238:613–614, which is incorporated herein by reference) Bjorkman, P. J. et al. *Nature* (suora). Soluble HLA-A can be purified after papain digestion of plasma membranes from the homozygous human lymphoblastoid cell line J-Y as described by Turner, M. J. et al., *J. Biol. Chem.* (1977) 252:7555–7567, all of which are incorporated herein by reference. Papain cleaves the 44 kd chain close to the transmembrane region yielding a molecule comprised of alpha$_1$, alpha$_2$, alpha$_3$, alpha$_2$, microglobulin A representation of the deduced three dimensional structure of the Class I HLA-A2 antigen is shown in FIG. 2.

While the three dimensional structure of Class II MHC antigens is not known in such detail, it is thought that Class II glycoproteins have a domain structure, including an antigen binding pocket, similar to that of Class I. It is formed from the N-terminal domain portions of two class II chains which extend from the membrane bilayer. The N-terminal portion of one chain has two domains of homology with the alpha$_1$ and alpha$_2$ regions of the MHC Class I antigen sequence. Cloning of the Class II genes (as described by Estees suora) permits manipulation of the Class II MHC binding domains for example, as described below.

The MHC glycoprotein portions of the complexes of the invention, then, can be obtained by isolation from lymphocytes and screened for the ability to bind the desired peptide antigen. The lymphocytes are from the species of individual which will be treated with the complexes. For example, they may be isolated from human B cells from an individual suffering from the targeted autoimmune disease, which have been immortalized by transformation with a replication deficient Epstein-Barr virus, utilizing techniques known in the art.

MHC glycoproteins have been isolated from a multiplicity of cells using a variety of techniques including solubilization by treatment with papain, by treatment with 3M KCl, and by treatment with detergent. In a preferred method detergent extraction of Class II protein from lymphocytes followed affinity purification is used. Detergent can then be removed by dialysis or selective binding beads, e.g., Bio Beads.

Alternatively, the amino acid sequence of a number of Class II proteins are known, and the genes have been cloned, therefore, the proteins can be made using recombinant methods. In a first generation synthetic MHC protein, the heavy (alpha) and light (beta) chains are synthesized using a carboxy terminal truncation which effects the deletion of the hydrophobic domain, and the carboxy termini can be arbitrarily chosen to facilitate the conjugation of toxins or label. For example, in the MHC protein shown in FIG. 3, lysine residues are introduced. In addition, cysteine residues near the carboxy termini are included to provide a means to form disulfide linkage of the chains; the synthetic gene can also include restriction sites to aid in insertion into expression vectors and in manipulating the gene sequence to encode analogs. The alpha and beta chains are then inserted into expression vectors, expressed separately in an appropriate host, such as *E. coli*, yeast, or other suitable cells, and the recombinant proteins obtained are recombined in the presence of the peptide antigen.

As the availability of the gene permits ready manipulation of the sequence, a second generation preferred construction includes hybrid Class I and Class II features, as illustrated in FIG. 4, wherein the alpha$_1$ and beta$_1$ domains of Class II MHC are linked through a flexible portion that permits intramolecular dimerization between these domains resulting in an edge-to-edge beta sheet contact. The beta$_1$ segment is then fused to the alpha$_2$ domain of Class I with beta$_2$ microglobulin coexpressed to stabilize the complex. The transmembrane and intracellular domains of the Class I gene can also be included but there may be no point in doing so unless liposomes are used to transport the complex. A simpler version includes only the alpha$_1$ and beta$_1$ domains with a C-terminal lysine for toxin conjugation (FIG. 4).

Construction of expression vectors and recombinant production from the appropriate DNA sequences are performed by methods known in the art per se.

Expression can be in procaryotic or eucaryotic systems. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, including such commonly used promoters as the beta-lactamase (penicillinase) and lactose (lac) promoter systems (Change et al., *Nature* (1977) 198:1056) and the tryptophan (trp) promoter system (Goeddel et al., *Nucleic Acids Res.* (1980) 8:4057) and the lambda-derived P$_L$ promoter and N-gene ribosome binding site (Shimatake et al., *Nature* (1981) 292:128). Any available promoter system compatible with procaryotes can be used. All references cited herein whether supra or infra, are hereby incorporated herein by reference.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al., *J. Biol. Chem.* (1980) 255:2073). Other promoters include those from the enolase gene (Holland, M. J., et al. *J. Biol. Chem.* (1981) 256:1385) or the Leu2 gene obtained from YEp13 (Broach, J., et al., *Gene* (1978) 8:121).

Suitable mammalian promoters include the early and late promoters from SV40 (Fiers, et al., *Nature* (1978) 273:113) or other viral promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and relegated in the form desired.

Site specific DNA cleavage is performed by treating with the suitable restriction enzyme (or enzymes) under conditions which are generally understood in the art, and the particulars of which are specified by the manufacturer or these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separation is found in Methods in Enzymology (1980) 65:499–560.

Restriction cleaved fragments may be blunt ended by treating with the large fragment of $E.$ $coli$ DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5-10 uM dNTPs. The Klenow fragment fills in a 5' sticky ends but chews back protruding 3' single strands, even through the four dNTPS, are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column.

Synthetic oligonucleotides are prepared using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1-2 mM ATP, 1.7 pmoles $^{32}P$-ATP (2.9 mCi/mmole), 0.1 mM spermidine, 0.1 mM EDTA.

Ligations are performed in 15–30 ul volumes under the following standard conditions and temperatures: 20 mM Tris-HCl pH 7.5, 10 mM $MgCl_2$, 10 mM DTT, 33 ug/ml BSA, 10 mM-50 mM NaCl, and either 40 uM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 ug/ml total DNA concentrations (5–100 nM total end concentration). Intermolecular blunt end ligations (usually employing a 10–30 fold molar excess of linkers) are performed at 1 uM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per ug of vector at 60° C. for about 1 hr. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a stand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming $E.$ $coli$ strain MM294 obtained from $E.$ $coli$ Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmid from the transformants are then prepared according to the method of Clewell, D. B., et al., $Proc.$ $Natl.$ $Acad.$ $Sci.$ $USA$ (1969) 62:1159, optionally following chloramphenicol amplification (Clewell, D. B., $J.$ $Bacteriol.$ (1972) 110:667. The isolated DNA is analyzed by restriction and/or sequenced by the dideoxy method of Sanger, F., et al., $Proc.$ $Natl.$ $Acad.$ $Sci.$ $USA$ (1977) 74:5463 as further described by Messing, et al., $Nucleic$ $Acids$ $Res.$ (1981) 9:309, or by the method of Maxam, et al., $Methods$ $in$ $Enzymology$ (1980) 65:499.

The constructed vector is then transformed into a suitable host for production of the protein.

Depending on the host cell used, transformation is done using standard techniques appropriate to such cells. The calcium treatment employing calcium chloride, as described by Cohen, S. N., $Proc.$ $Natl.$ $Acad.$ $Sci.$ $USA$ (1972) 69:2110, or the RbCl method described in Maniatis, et al., $Molecular$ $Cloning:$ $A$ $Laboratory$ $Manual$ (1982) Cold Spring Harbor Press, p. 254 is used for procaryotes or other cells which contain substantial cell wall barriers. For mammalian cells without such cell walls, the calcium phosphate precipitation method of Graham and van der Eb, *Virology* (1978) 52:546 or electroporation is preferred. Transformations into yeast are carried out according to the method of Van Solingen, P., et al., *J. Bacter.* (1977) 130:946 and Hsiao, C. L., et al., *Proc. Natl. Acad. Sci. USA* (1979) 76:3829.

The transformed cells are then cultured under conditions favoring expression of the MHC sequence and the recombinantly produced protein recovered from the culture.

ANTIGENIC PEPTIDES

The autoantigenic proteins or tissues for a number of autoimmune diseases are known. For example, experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis (Stuart et al. (1984), *Ann. Rev. Immunol.* 2:199-218; van Eden et al 1988), *Nature* 331:171-173.); thyroglobulin has been identified in experimental allergic thyroiditis (EAT) in mouse (Maron et al. (1988), *J. Exp. Med.* 152:1115-1120); acetyl choline receptor (AChR) in experimental allergic myasthenia gravis (EAMG) (Lindstrom et al. (1988), *Adv. Immunol.* 42:233-284); and myelin basic protein (MBP) and proteolipid protein (PLP) in experimental allergic encephalomyelitis (EAE) in mouse and rat (See Acha-Orbea et al., supra). In addition, for example, target antigens have been identified in humans: type-II collagen in human rheumatoid arthritis (Holoshitz et al. (1986), *Lancet* ii:305-309); and acetyl choline receptor in myasthenia gravis (Lindstrom et al. (1988), supra) all of the above are incorporated herein by reference.

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These segments are supposed to be 8-151 units in length, and contain both the agretope and the epitope recognized by the T-helper cell. The epitope itself is a contiguous or non-contiguous sequence of 5-6 amino acids which recognizes the antigen-specific receptor of T-helper cells; the agretope is a continuous or non-contiguous sequence which is responsible for the association of the peptide with the MHC glycoproteins.

The empirical process of determining the relevant 8-15 amino acid subunits is illustrated using the alpha subunit of the acetylcholine receptor of skeletal muscle. In myasthenia gravis (MG) an autoimmune response is directed to a region of this subunit. A loss of the acetyl choline receptors on the postsynaptic membrane of the neuromuscular junction causes the MG symptoms.

In MG autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc. Natl. Acad. Sci. USA* (1980) 77:755). The peptide segments recognized by autoreactive human T-cells also are located on the alpha subunit (Hohfield, et al., *Proc. Natl. Acad. Sci. USA* (1987). The epitopes recognized by these T-cells lie between residues 1-30, 125-147, 169-181, 257-271 and 351-368. In addition, in humans the AChR peptides 195-212 and 257-269 have been partially characterized as epitopes in myasthenia gravis patients of the HLA-DR5 and HLA-DR3, DQw2 MHC haplotypes, respectively (See Acha-Orbea (1989), supra).

The peptides carrying agretopes permitting presentation of the epitopes associated with alpha subunit of this receptor are determined as follows.

Figure 5:
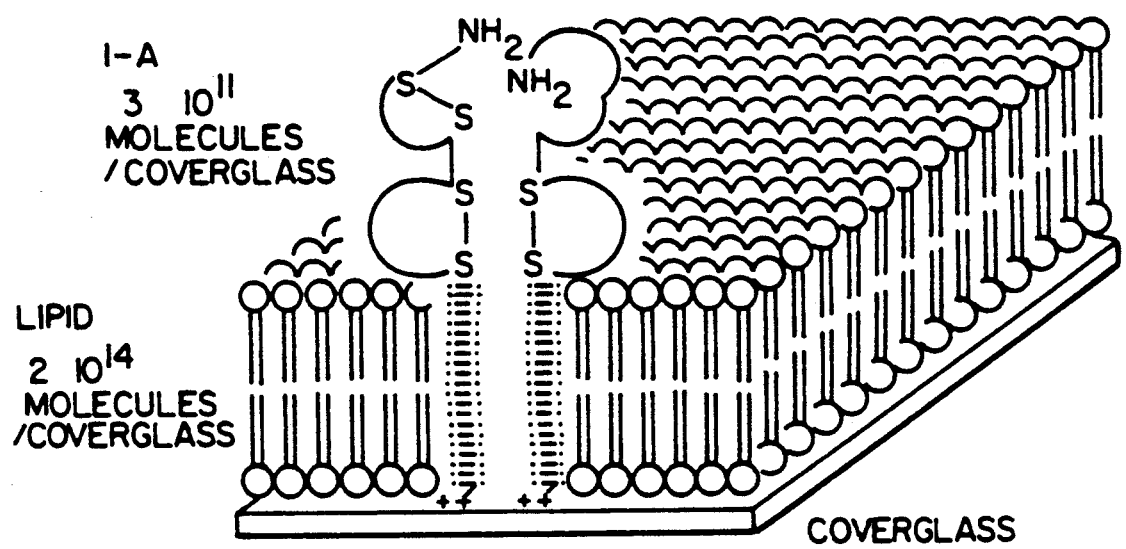

Strains of mice which when immunized with Torpedo californicus AChR, develop a disease with many of the features of human myesthenia gravis are used as model. MHC Class II glycoproteins are isolated from spleen cells of mice of this strain using lectin and monoclonal antibody affinity supports. The purified MHC Class II proteins are incorporated into phospholipid vesicles by detergent dialysis. The resultant vesicles are then allowed to fuse to clean glass cover slips to produce on each a planar lipid bilayer containing MHC molecules as shown in FIG. 5 (Brian and McConnell, *Proc. Natl. Acad. Sci. USA* (1984) 81:6159, which is incorporated herein by reference).

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and PBS and allowed to incubate several days. The extent of binding of peptide in the MHC Class II glycoprotein antigen binding pocket is measured by the amount of radio-activity incorporated into the MHC Class II-planar lipid membrane on the cover slip versus planar lipid membrane alone. Specific incorporation of radioactivity indicates that the bound peptide contains an agretope MHC Class II peptide binding site) of one of the several species of MHC Class II molecules present in the planar lipid membrane. In this way, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the antigen binding pocket of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well. T-cell proliferation, as measured by tritiated thymidine uptake into DNA, indicates that the MHC Class II protein-bound peptide contains both an agretope and an epitope for binding to the T-cell.

The Dupont apparatus and technique for raoid multiple peptide synthesis (RAMPS) is used to synthesize the members of a set of overlapping (10 residue overlap), 20-residue peptides from the alpha subunit of Torpedo californicus AChR. The sequence of this peptide is known and is shown in FIG. 6. One or more radioactive amino acids is incorporated into each synthetic peptide. The pentafluorphenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively the overlapping sequences which include the putative segments of 8-15 amino acids of the antigenic protein, such as acetylcholine receptor protein, can be synthesized on the method of Geysen, H. M., et al. *J. Immun. Meth.* (1987) 102:274, which is incorporated herein by reference. The synthesized radio labeled peptides are tested by incubating them individually (on the plates) with purified MHC proteins which have been formulated into lipid membrane bilayers as above.

In multiple sclerosis (MS), which results in the destruction of the myelin sheath in the central nervous system, myelin basic protein (MBP), the major protein component of myelin is the principal autoantigen. Pertinent segments of the MBP protein are also determined empirically, using a strain of mice which develops experimental allergic encephalitis (EAG) when immunized with bovine myelin basic protein, the sequence of MBP is shown in FIG. 7.

Systemic lupus erythematosus (SLE) has a complex systemology, but results from an autoimmune response to red blood cells. Peptides which are the antigenic effectors of this disease are found in the proteins on the surface of red blood cells.

Rheumatoid arthritis (RA) is a chronic inflammatory disease resulting from an immune response to proteins found in the synovial fluid.

Insulin-dependent diabetes mellitus (IDDM) results from autoimmune attack on the beta cells within the Islets of Langerhans which are responsible for secretion of insulin. Circulating antibodies to Islets cells surface antigens and to insulin are known to precede IDDM. Critical peptides in eliciting the immune response in IDDM are believed to be portions of the insulin sequence and the Islet's surface proteins.

The relevant antigenic peptide subunits, as they are relatively short, can readily by synthesized using standard automated methods for peptide synthesis. In the alternative, they can be made recombinantly using isolated or synthetic DNA sequences; though this is not the most efficient approach for peptides of this length.

Thus, in summary, a set of labeled test peptides is prepared, and those which bind to MHC in planar lipid membranes containing MHC proteins are shown to contain the agretope.

The identified peptides are then prepared by conventional solid phase synthesis and the subset which contain epitopes for the disease-inducing helper T-cell clones i determined by incubation of the candidate peptides with murine antigen-presenting cells (APC) (or with isolated MHC complex) and spleen or lymph node T-cells from mice immunized with the full length protein. Successful candidates will stimulate T-cell proliferation in this system. This second, smaller, subset represents the suitable peptide component.

THE EFFECTOR COMPONENT

In one embodiment, the complexes of the invention are designed to destroy the immune response to the peptide in question. In this instance, the effector portion of the molecule will be, for example, a toxin, a chemotherapeutic agent, an antibody to a cytotoxic T-cell surface molecule, a lipase, or a radioisotope emitting "hard" e.g., beta radiation. For example, a number of protein toxins are well known in the art including ricin, diphtheria, gelonin, Pseudomonas toxin, and abrin. Chemotherapeutic agents include, for example, doxorubicin, daunorubicin, methotrexate, cytotoxin, and antisense RNA. Antibiotics can also be used. Antibodies have been isolated to cytotoxic T-cell surface molecules and these may thus operate as toxins. In addition, radioisotopes such as yttrium-90, phosphorus-32, lead-212, iodine-131, or palladium-109 can be used. The emitted radiation effects the destruction of the target T-cells.

In some cases the active portion of the effector component is entrapped in a delivery system such as a liposome or dextran carrier; in these cases, either the active component or the carrier may be bound in the complex.

If the effector molecule is intended to be a label, a gamma-emitting radioisotope such as technetium-99 or indium-111 can be used. In addition, other types of labeling such as fluorescence labeling by, for example, fluorescein can be used.

The effector component can be attached to the MHC glycoprotein as shown in FIG. 2, or, if its nature is suitable, to the peptide portion. For example, iodine 131 or other radioactive label can often be included in the peptide determinant sequence.

FORMATION OF THE COMPLEX

The elements of the complex can be associated by standard means known in the art. For example, protein toxins can be conjugated to the MHC-derived protein by standard dehydration reactions using carbodiimides or by heterobifunctional linkers. The antigenic peptides can be associated noncovalently with the pocket portion of the MHC protein, or they too can be covalently bound using standard procedures by, for example, photo affinity labelling, (see e.g., Hall et al., *Biochemistry* 24:5702-5711 (1985), which is incorporated herein by reference).

The sequence of preparing the complex depends on the components in each instance. For example, in a particular protocol, the peptide portion and MHC portion are noncovalently associated by contacting the peptide with the MHC component, e.g., by mixing and the effector is then covalently linked, if desired using commercially available linkers, such as SPDP (Pierce Chemicals) to the MHC. Alternatively, the effector and MHC may be first conjugated using a dehydration reaction and the conjugate complexed with the peptide component.

If the effector is itself a protein, the entire complex may be made directly from the appropriate encoding DNA using recombinant methods. For example, the AChR peptide 195-215, which has been characterized as an epitope in MG in humans and in mice, may be connected to the N-terminal end of a polypeptide derived from an MHC antigen associated with MG. The amino acid sequence of the AChR peptide in one letter amino acid code is:

DTPYLDITYHFIMQRIPLYFV

An oligonucleotide which encodes the peptide is synthesized using the known codons for the amino acid, preferably those codons which have preferred utilization in the organism which is to be used for expression are utilized in designing the oligonucleotide. Preferred codon utilizations for a variety of organisms and types of cells are known in the art. If, for example, expression is to be in *E. coli.* a suitable oligonucleotide sequence encoding AChR 195-215 could be:

5' GAC ACC CCG TAC CTG GAC ATC ACC TAC CAC TTC ATC

ATG CAG CGT ATC CCG CTG TAC TTC CTG 3'.

This sequence may then be incorporated into a sequence encoding the peptides derived from the MHC antigen, utilizing techniques known in the art. The incorporation site will be such that, when the molecule is expressed and folded, the AChR peptide antigen will be available as an epitope for the target T cells.

In one protocol, the AChR 195-215 peptide is attached to the N-terminal end of the appropriate MHC molecule. If the recombinant complex is to be used in mice, for example, the AChR peptide may be incorporated into a sequence encoding either the I-$A^b$-alpha or I-$A^b$-beta chain. The sequences encoding these chains are known, and are shown in FIG. 8 (alpha chain), and FIG. 9 (beta chain); also shown in the figures are restriction enzyme sites and significant domains of the chains. If the AChR peptide is to be incorporated into the beta chain, for example, the oligonucleotide may be inserted as a replacement for the leader peptide. Methods of replacing sequences within polynucleotides are known in the art, examples of which are described in the section on the construction of plasmids.

A similar protocol may be used for incorporation of the AChR peptide into a sequence encoding a peptide derived from the appropriate human HLA antigen. For example, in humans, the haplotype DR2W2 is associated with MG. Hence, the AChR peptide may be incorporated into, for example, a sequence encoding a beta-chain of a DR2 allele. The structural basis in the DR subregion for the major serological specificities DR-19 are known, as are the sequences encoding the HLA-DR-beta chains from a number of DR haplotypes. See, for e.g., Bell et al. (1987), *Proc. Natl. Acad. Sci. USA* 84:6234-6238 which are incorporated herein by reference.

As demonstrated above, the autoimmune antigen peptide and the MHC component may be linked via peptide linkages. However, other modes of linkage are obvious to those of skill in the art, and could include, for example, attachment via carbohydrate groups on the glycoproteins, including, e.g., the carbohydrate moieties of the alpha-and/or beta-chains.

ASSESSMENT OF THE COMPLEX

The complexes of the invention can be assayed using an in vitro system or using an in vivo model. In the in vitro system, the complex is incubated with peripheral blood T-cells from subjects immunized with the protein or antigen responsible for the condition associated with the peptide of the complex. The successful complexes will prevent further proliferation of the antigen specific T-cells even upon stimulation with additional antigen.

In the in vivo system, T-cells that proliferate in response to the isolated epitope or to the full length antigen in the presence of APC are cloned. The clones are injected into histocompatible animals which have not been immunized in order to induce the autoimmune disease. Symptoms related to the relevant complex should ameliorate or eliminate the symptoms of the disease.

Either of the types of complexes, i.e., with or without the effector component, may be used. In a preferred mode the treatment is two-fold. The individual is treated with the complex of MHC-encoded antigen-presenting glycoprotein containing an effective portion of the antigen to down-regulate the immune system. Further down-regulation is achieved by treatment with the three component complex with includes the MHC-encoded antigen-presenting glycoprotein, an effective portion of antigen which is specific for the autoimmune disease being treated, and an effector component. In addition, panels of complexes may be used for treatment. For example, if it is suspected that more than one peptide of an antigen is involved in the autoimmune response, and/or if it is suspected that more than one antigen is involved, the individual may be treated with several complexes selected from a panel containing the appropriate MHC-encoded antigen-presenting polypeptides, and effective portions of antigens; these may be with or without effector components.

Administration of a labeled complex permits identification of those portions of the immune system involved in the disease, in diagnostic applications.

SELECTION OF THE MHC COMPLEXES FOR THERAPY AND/OR DIAGNOSIS

In order to select the MHC complexes of the invention which are to be used in the diagnosis or treatment of an individual for an autoimmune disease, the type of MHC antigens which are involved in the presentation of the autoantigen are identified.

Specific autoimmune disfunctions are correlated with specific MHC types. A list of the DQ/DR haplotypes in humans and their associations with autoimmune diseases are shown in FIG. 10. Methods for identifying which alleles, and subsequently which MHC encoded polypeptides, are associated with an autoimmune disease are known in the art. A method described in EP 286447 is suitable. In this method several steps are followed. First, the association between an MHC antigen and the autoimmune disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease (See FIG. 10).

Second, specific alleles encoding the disease associated with MHC antigen/polypeptide are identified. In the identification of the alleles, it is assumed that the susceptibility allele is dominant. Identification of the allele is accomplished by determining the strong positive association of a specific subtype with the disease. This may be accomplished in a number of ways, all of which are known to those skilled in the art. E.g., subtyping may be accomplished by mixed lymphocyte response (MLR) typing and by primed lymphocyte testing (PLT). Both methods are described in Weir and Blackwell, eds., Handbook of Experimental Immunology, which is incorporated herein by reference. It may also be accomplished by analyzing DNA restriction fragment length polymorphism (RFLP) using DNA probes that are specific for the MHC locus being examined. E.g., Nepom (1986), Annals N.Y. Acad. Sci. 475, 1. Methods for preparing probes for the MHC loci are known to those skilled in the art. See, e.g., Gregersen et al. (1986), *Proc. Natl. Acad. Sci. USA* 79:5966; Weissman et al. in *Medicine in Transition: the Centennial of the University of Illinois College of Medicine* (E. P. Cohen, ed. 1981) all of which are incorporated herein by reference.

The most complete identification of subtypes conferring disease susceptibility is accomplished by sequencing of genomic DNA of the locus, or cDNA to mRNA encoded within the locus. The DNA which is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique.

Once the allele which confers susceptibility to the specific autoimmune disease is identified, the polypeptide encoded within the allele is also identifiable, i.e., the polypeptide sequence may be deduced from the sequence of DNA within the allele encoding it. The MHC antigen complexes of the invention used for diagnosis and/or therapy are derived from the MHC antigen associated with the autoimmune disease state and from an autoimmune antigen associated with the same disease state.

As an example, over 90% of rheumatoid arthritis patients have a haplotype of Dw4 or Dw14 (See FIG. 10). It is also known that a target antigen in human rheumatoid arthritis is type-II collagen. Hence, the complexes of the invention used for treatment or diagnosis of an individual with rheumatoid arthritis would include those containing a polypeptide derived from the Dw4 and/or Dw14 which is capable of antigen presentation, complexed with an effective portion of type-II collagen.

A protocol which may be suitable for the utilization of the complexes of the invention for the diagnosis and/or treatment of an autoimmune disease is depicted in FIG. 11. Briefly, an individual having (or susceptible to) an autoimmune disease is identified, and the autoimmune disfunction is identified. Identification may be by symptomology and/or an examination of family histories. The individual's MHC type is determined by one or more of several methods known in the art, including, for example, cell typing by MLR, by serologic assay, and by DNA analysis (including RFLP and PCR techniques). The individuals T cells are examined in vitro, to determine the autopeptide(s) recognized by autoreactive T cells; this is accomplished utilizing labeled complexes of the invention, described supra., which are of the formula X-MHC-peptide (wherein X is a label moiety. After it is determined which complexes target the T-cells, the individual is treated with complexes of the invention which are able to suppress the specific autoreactive T-cell replication and/or those which kill the autoreactive T-cells; these are complexes of the type MHC-peptide, and, X-MHC-peptide (wherein X is a moiety capable of killing the T-cell), respectively. Therapy (as determined by the autoreactive T-cells remaining) is monitored with T-cell binding studies using the labeled complexes of the invention, described supra.

As used herein, the term "individual" encompasses all mammals and probably all vertebrates which possess basically equivalent NHC systems.

MODEL SYSTEMS FOR IN VIVO TESTING

The following are model systems for autoimmune diseases which can be used to evaluate the effects of the complexes of the invention on these conditions.

Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al., *J. Exp. Med.* (1978) 147:1653, which is incorporated hereby by reference.

In both the human and murine forms of the disease, a strong association with NHC gene products has been reported. HLA-DR2 and HLA-DR3 individuals are at a higher risk than the general population to develop SLE (Reinertsen, et al., *N. Engl. J. Med* (1970) 299:515), while in NZB/W $F_1$ mice ($H-2^{d/u}$), a gene linked to the $h-2^u$ haplotype derived from the NZW parent contributes to the development of the lupus-like nephritis.

The effect of the invention complex can be measured by survival rates and by the progress of development of the symptoms, such as proteinuria and appearance of anti-DNA antibodies.

Proteinuria is measured colorimetrically by the use of Uristix (Miles Laboratories, Inc., Elkhart, IN), giving an approximation of proteinuria as follows: trace, 10 mg/dl; 1+, 30 mg/dl; 100mg/dl; 3+, 300 mg/dl; and 4+, 1000 mg/dl. The development of high grade proteinuria is significantly delayed by treatment of the mice with complex.

The presence of anti-DNA specific antibodies in NZB/W $F_1$ mice is determined by using a modification of a linked immunosorbent assay (ELISA) described by Zouali and Stollar, *J. Immunol. Methods* (1986) 90:105 which is incorporated herein by reference.

Myasthenia Gravis (MG)

Myasthenia gravis is one of several human autoimmune diseases linked to HLA-D. Safenberg, et al., *Tissue Antigens* (1978) 12:136; McDevitt, et al., *Arth. Rheum.* (1977) 20:59 which are incorporated herein by reference. In MG antibodies to the acetyl choline receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the region within H-2. Christadoss, et al., *J. Immunol.* (1979) 123:2540.

AcChoR protein is purified from Toroedo californica and assayed according to the method of Waldor, et al., *Proc. Natl. Acad. Sci.* (USA) (1983) 80:2713, incorporated by reference. Emulsified AcChoR, 15 ug in complete Freund adjuvant, is injected intradermally among six sites on the back, the hind foot pads, and the base of the tail. Animals are reimmunized with this same regimen 4 weeks later.

Evaluation can be made by measurement of anti-AcChoR antibodies. Anti-AcChoR antibody levels are measured by a microtiter ELISA assay as described in Waldor, et al., supra. The standard reagent volume is 50 ul per well. Reagents are usually incubated in the wells for 2 hr at RT. Five ug of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% $NaN_3$. Mouse sera are diluted in 0.01M PBS (pH 7.2), 1.5 mfr $MgCl_2$, 2.0 mM 2-mercaptoethanol, 0.05% Tween-80, 0.05% $NaN_3$ (p-Tween buffer) and incubated on the plate. After the plate is washed, beta-galactosidase-conjugated sheep anti-mouse antibody diluted in P-Tween buffer is added to each well. After a final washing, the enzyme substrate, p-nitrophenylgalctopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with complex is expected to significantly reduce the titer of anti-AcChoR antibodies in the immunized mice.

The effect of treatment with complex on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of complex.

Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion. Huse, et al., *Fed. Proc.* (1984) 43:1820.

Mice from a susceptible strain, DEA-1 are caused to have CIA by treatment of the mice with native type II collagen, using the technique described in Wooley and Luthra, *J. Immunol.* (1985) 134:2366, incorporated herein by reference.

In another model adjuvant arthritis in rats is an experimental model for human arthritis, and a prototype of autoimmune arthritis triggered by bacterial antigens, Holoschitz, et al., *Prospects of Immunology* (CRC Press) (1986); pearson *Arthritis Rheum.* (1964) 7:80. The disease the result of a cell-mediated immune response, as evidenced by its transmissibility by a clone of T-cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, supra, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The effect of complex treatment of manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDOM populations, and by clinical associations between IDDM and various autoimmune diseases. An animal model for spontaneous IDDM and thyroiditis has been developed in the BB rat. As in humans, the rat disease is controlled in part by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat. Biotard, et al., *Proc. Natl. Acad. Sci. USA* (1985) 82:6627.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle call change. See Biotard et al. Supra.

Treatment of the BB rats with complex of the invention is expected to ameliorate or prevent the manifestation of the clinical and morphological symptoms associated with IDDM and thyroiditis.

In another model, the NOD mouse strain ($H-2K^dD^b$) is a murine model for autoimmune IDDM. The disease in these animals is characterized by anti-islet cell antibodies, severe insulitis, and evidence for autoimmune destruction of the beta-cells. Kanazawa, et al., *Diabetolooia* (1984) 27:113. The disease can be passively transferred with lymphocytes and prevented by treatment with cyclosporin-A (Ikehara, et al., *Proc. Natl. Acad. Sci. USA* (1985) 82:7743; Mori, et al.), *Diabetolooia* (1986) 29:244. Untreated animals develop profound glucose intolerance and ketosis and succumb within weeks of the onset of the disease. Seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to $I-A_B$. Acha-Orbea and McDevitt, *Proc. Natl. Acad. Sci. USA* (1907) 84:235.

Treatment of Female NOD mice with complex is expected to lengthen the time before the onset of diabetes and/or to ameliorate or prevent the disease.

EXPERIMENTAL ALLERGIC ENCEPHALOMYELITIS (EAE)

Experimental allergic encephalomyelitis (EAE) is an induced autoimmune disease of the central nervous system which mimics in many respects the human disease of multiple sclerosis (MS). The disease can be induced in many species, including mice and rats.

The disease is characterized by the acute onset of paralysis. Perivascular infiltration by mononuclear cells in the CNS is observed in both mice and rats. Methods of inducing the disease, as well as symptomology, are reviewed in Aranson (1985) in *The Autoimmune Diseases* (eds. Rose and Mackay, Academic Press, Inc.) pp. 399–427, and in Acha-Orbea et al. (1989), *Ann. Rev. Imm.* 7:377–405.

One of the genes mediating susceptibility is localized in the MHC class II region (Moore et al. (1980), *J. Immunol.* 124:1815–1820). The best analyzed encephalitogenic protein is myelin basic protein (MBP), but other encephalitogenic antigens are found in the brain. The immunogenic epitopes have been mapped (see Acha-Orbea et al., supra.). In the PL mouse strains (H-$2^u$) two encephalitogenic peptides in MBP have been characterized: MBP peptide p35-47 (MBP 35-47), and acetylated NSF p1-9 (MBP 1-9).

The effect of the invention complexes on ameliorating disease symptoms in individuals in which EAE has been induced can be measured by survival rates, and by the progress of the development of symptoms.

FORMULATION AND ADMINISTRATION

The complexes of the invention are conveniently administered in the form of liposomes or micelles if the transdermal region of the MHC is included. Liposomes can be prepared according to standard methods, as described in, e.g., Szoka et al. *Ann. Rev. Biophys. Bibliog.* 9:467 (1980) and U.S. Pat. Nos. 4,235,871; 4,501,728; and 4,837,028 all of which are incorporated herein by reference. However, if the transdermal region is deleted, the complex can be administered in a manner conventionally used for peptide-containing pharmaceuticals. Administration is systemic and is effected by injection, preferably intravenous, thus formulations compatible with the injection route of administration may be used. Suitable formulations are found in *Remington's Pharmaceutical Sciences*, Mack Publishing Company, Philadelphia, Pa., 17th ed. (1985), which is incorporated herein by reference. A variety of pharmaceutical compositions comprising complexes of the present invention and pharmaceutically effective carriers can be prepared. The pharmaceutical compositions are suitable in a variety of drug delivery systems. For a brief review of present methods of drug delivery, see, Langer, *Science* 249:1527–1533 (1990) which is incorporated herein by reference. A dosage level of 10–500 ug for murine subjects is effective; thus about 0.5 mg/kg to 25 mg/kg is suggested.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration which comprise a solution of the complex dissolved or suspended in an acceptable carrier, preferably an aqueous carrier. A variety of aqueous carriers may be used, e.g., water, buffered water, 0.4% saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. As described above, the complexes may be delivered via liposome preparations.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%-20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the complexes of the invention are administered to a patient susceptible to or otherwise at risk of a particular disease. Such an amount is defined to be a "prophylactically effective dose." In this use, the precise amounts again depend on the patient's state of health and weight.

The following examples illustrate, but do not limit, the invention.

EXAMPLE I

Preparation of Labeled (1–131) MHCII-BMBP Peptide Complex

An iodinated synthetic peptide representing amino acids 1–13 of bovine myelin-basic protein (BNBP) is synthesized using standard solid phase synthesis for FMOC protected amino acids. The resulting peptide has the sequence Ac-Ala-Ser-Ala-Gln-Lys-Arg-Pro-Ser-Gln-Arg-Ser-Lys-(I-131)Tyr-NH$_2$. MHCII is purified from spleen cells of PL/J strain mice according to the method of Turkewltz et al. (supra) incorporated herein by reference. The purified MHCII in detergent or as a lipid bilayer (suora) is incubated with the synthesized peptide until the radiolabel uptake into the high molecular weight fraction is optimized. The excess radiolabeled peptide is then removed by dialysis or gel filtration and the resulting complex is dialyzed in the presence of lipid to form micelles.

EXAMPLE 2

Use of MHCII-BMBP 131-I as a Toxin

Cloned T-helper cells specific for the N-terminal 13 amino acid sequence of BMBP are obtained from PL/J strain mice immunized with BMBP, by the method of Steinman. The isolated cloned T-helper cells are incubated with the complex prepared in Example 1 at a concentration of $10^6$ cells/ml and 0.1–1.0 ug/ml of the complex for 4–16 hours and 37° C.

The cells are washed and cell survival of the T-lymphocytes is then determined on washed cells. The culture is incubated with concanavalin A and the uptake of tritiated thymidine assessed as an index of T-helper cell survival and proliferation.

The survival of cells after treatment with the radiolabeled complex and in the presence of BMBP and autologous antigen-presenting cells is less than 50% of that of cells incubated with nonlabeled complex or incubated in the presence of tritiated thymidine without BMBP.

EXAMPLE 3

Down-Regulation of T-Cells In Vitro With A Complex of Mouse I-A$^k$ and rat MBP Peptide The efficacy of Class II MHC-peptide complexes in induction of nonresponsiveness in T-cell clones directed against epitopes of myelin basic protein (MBP), known to induce experimental allergic encephalomyelitis in mice, a disease model which mimics human multiple sclerosis, is shown below.

T-cell clones AJ1.2 and 4R3.4 prepared by immunization of mice against rat MBP peptide (1–11) and characterized for antigen specificity were obtained from Dr. Pat Jones of Stanford University.

The I-A$^k$ complex with rat NSF peptide was formed utilizing purified mouse I-A$^k$ and synthetic rat MBP peptide (1–13), the sequence for which is known (Zamvil et al. (1986), *Nature* 324:258260), and which is:

*Ac-ASQKRPSQRHGSK*

Mouse I-A$^k$ was purified by a modified method based upon Turkewitz et al. (1903), supra. Basically, a soluble membrane extract of cells containing I-A$^k$ was prepared using NP-40. I-A$^k$ from the extract was purified by affinity chromatography, using a column containing 10–2.16 antibodies, which had been purified by affinity chromatography on Protein-A, and which were coupled to CNBr activated Sepharose 4b. The preparation schemes for the NP-40 soluble membrane extract, for the purification of 10–2.16 Mab and its coupling to CnBr activated Sepharose 4B, and for the purification of I-A$^k$, are shown in FIGS. 12, 13a and 14, respectively. FIG. 13b is a copy of a polyacrylamide gel showing the Purity of the purified 10–2.16 antibody. The purity of I-A$^k$, as monitored by polyacrylamide gel analysis, is shown in FIG. 15.

In order to form the complex of I-A$^k$ and rat MBP peptide, ten ug of affinity-purified I-A$^k$ in PBS containing 30 mM octyl qlucoside and 50-fold molar excess of HPLC-purified MBP peptide were mixed in a total volume of 125 ul Samples were incubated at 37° C. for 16 hours with constant shaking and were either separated from peptide by G-24 Sephadex desalting for liposome preparation or, for cell studies, were dialyzed against PBS followed by RPMI media for 36 hours at 4° C.

The introduction of the I-A$^k$-MBP peptide complex into liposomes was as follows. A lipid solution consisting of cholesterol:dipalmitoylphosphatidyl choline (DPPC):dipalmitoylphosphatidyl ethanolamine-fluorescein (DPPEF) at a molar ration of 25:75:2 was prepared in chloroform containing 30 mM octyl glucoside (OG). Lipid was dried under vacuum and preformed I-A$^k$-peptide complex in PBS containing 17 mM OG was mixed with dried lipid at a ration of 5:1 (w/w). The mixture was vortexed for 2–3 minutes, cooled to 4° C., and finally dialyzed against PBS followed by RPMI media for 36 at 4° C. In experiments using (125-I)-labeled I-A$^k$, no fluoresceinated lipid was included in the lipid mixture, and the incorporation of I-A$^k$ into liposomes was measured by scintigraphy.

Planar lipid membranes were prepared on sterile 12 mm glass coverslips using 50–100 ul of liposomes containing affinity-purified I-A$^k$ alone or purified I-A$^k$+MBP(1–13) by the method of Watts et al. (1985), *Proc. Natl. Acad. Sci. USA* 82:5480–5484, which is incorporated herein by reference. The presence of I-A$^k$ in planar membranes was confirmed by fluorescence microscopy after staining with fluorescent anti-I-A$^k$ antibody. No fluorescence above background was noted upon staining with fluorescent anti-I-A$^d$.

AJ1.2 and 4R3.4 cells obtained six to eight days after MBP peptide stimulation were washed twice, and the $4 \times 10^5$ cells were added to planar membranes. The plates were incubated for 48-72 hours in 5% $CO_2$ at 37° C. and then examined visually for formation of colonies.

The effects of detergent-solubilized Class II molecules were examined by culturing $1 \times 10^5$ AJ1.2 or 4R3.4 cells with 50-100 ul of purified I-$A^k$ alone, purified I-$A^k$ plus MBP(1-13) and medium alone for five hours at 37° C. in 5% $CO_2$. Following this incubation the cells were diluted to 900 ul and tested for their ability to respond to antigen-presenting cells (APC) and antigen [MBP(1-13)] in a proliferation assay. Uptake of 3-(4,5-dimethyl-thiazol-2-7')-2,5 diphenyltetrazolium bromide (MTT) was used as an indication of cell proliferation. Although DNA synthesis, usually monitored by $^3$H-thymidine uptake, and the activity of mitochondria, measured by MTT uptake, are different cellular functions, it has been demonstrated that these two activities, monitored three days after initiation of stimulation of spleen cell cultures, tracked each other very well (Molecular Device Application Bulletin Number 011-A, Feb. 9, 1988).

Data are presented as % suppression of proliferation of cells incubated with Class I +Ag compared to cells cultured with medium alone and were calculated by using the formula:

$$\frac{(O.D.)570 \, [T \, cells_a + Spleen \, cells + MBP(1-11)] - (O.D.)570[T \, cells_b + Spleen \, cells]}{(O.D.)570 \, [T \, cells_c + Spleen \, cells + MBP(1-13)] - (O.D.)570[T \, cells_c + Spleen \, cells]}$$

wherein

T cells$_a$ = T cells preincubated with I-$A^k$-MBP(1-13) complex

T cells$_b$ = T cells preincubated with I-$A^k$-MBP(1-13) alone

T cells$_c$ = T cells preincubated with medium.

Since proliferation of cells cultured in the presence of Class II MHC alone was generally equal to cells cultured with medium alone in most studies, this latter number was used in obtaining % suppression. The Standard Deviation of triplicate wells was <10% in the majority of experiments.

Initially two qualitative studies were performed to determine whether pretreatment with I-$A^k$+MBP(1-13) will alter the binding of T cell clones to planar membranes prepared from liposomes containing I-$A^k$+MBP(1-13). AJ1.2 cells were used for these studies because they formed characteristic colonies on planar membranes in the presence of MBP(1-13) alone, i.e., without antigen presenting cells APC). Preincubation of AJ1.2 cells with I-$A^k$+MBP(1-13) for five hours inhibited the number of colonies formed on planar membranes compared to cells incubated with I-$A^k$ or medium alone. In the second experiment, AJ1.2 cells were incubated with liposomes containing I-$A^k$+MBp(1-13) or with I-$A^k$ alone for five hours and then added to planar membranes prepared as described above. As noted previously with detergent-solubilized I-$A^k$ MBP(1-13), culturing of cells with liposome containing I-$A^k$+MBP(1-13) reduced the number of colonies in comparison to cells incubated with liposomes containing I-$A^k$ alone. Although colonies could not be counted accurately, clear differences in their number were evident.

Because these studies did not allow quantitation of the effects of I-$A^k$+MBP(1-13) on the function of T cell clones, we examined the effects of preincubation with this complex on the proliferation of 4R3.4 or AJ1.2 cells in the presence of APCs and MBP(1-13). Therefore, 4R3.4 or AJ1.2 cells were preincubated with 50-100 ul of I-$A^k$+MBP(1-13), IA$^k$, or medium alone for five hours at 37° C. The cells were then diluted to an appropriate concentration and added to APC. Antigen [MBP(1-13)] was added to a final concentration ranging from 13.3 um to 53.2 um.

APC used in the study were prepared from spleens of female A/J mice. Briefly, spleens were removed and single cell suspensions were prepared by gentle teasing between the frosted ends of sterile microscope slides. Red cells were lysed by hypotonic shock. The remaining cells were washed twice with RPMI containing antibiotics and incubated with 10 micrograms/ml mitomycin-C for 1 hour at 37° C. Following this incubation, spleen cells were washed five times with RPMI containing antibiotics, counted, and used as APC's.

Following a 72-hour incubation period of the cells with APC and MBP(1-13), the extent of proliferation was quantitated using MTT uptake. The results of eight such studies are summarized in FIG. 16. In studies 1, 3, and 4, 4R3.4 cells were incubated as above. In study 2, 4R3.4 cells were preincubated with liposomes containing I-$A^k$+MBP(1-13) or I-$A^k$ alone. T cells were then separated from unbound liposomes by centrifugation through a 10% Ficoll solution, washed, and used in proliferation assays. Studies 5 through 8 were carried out with the clone AJ1.2. Cells incubated with I-$A^k$ alone proliferated to the same extent as cells cultured in medium. T cell clones preincubated in this manner did not proliferate in the absence of APC.

The data presented above demonstrate that the complex of Class II MHC+MBP(1-13) induces dramatic nonresponsiveness in T cell clones specific for MBP(1-11). In addition, the data show that this complex was immunologically reactive with, and hence bound to the MBP-stimulated T-cell clones.

EXAMPLE 4

Induction of EAE in Mice

Adoptive transfer of T cell clones AJ1.2 and 4R3.4, as well as immunization of mice with MBP(1-13) causes mice to develop EAE.

EAE with the peptide was induced using the method for induction of EAE in mice with intact MBP. Briefly, MBP(1-13 was dissolved in PBS and mixed vigorously with complete Freund's adjuvant so as to form a thick emulsion. Female A/J mice were injected with 100 micrograms of this mixture at four sites on the flank. Twenty-four and 72 hours later, 400 ng of pertussis toxin was injected intravenously. Mice are observed daily by two individuals for the development of EAE and mortality. The results in FIG. 17 show the development of EAE in mice resulting from immunization with MBP(1-13).

For the adoptive transfer of EAE, T cell clone 4R3.4, obtained from B10A(4R) strain of mice following immunization with MBP(1-11) was used. B10.A(4R) mice were given 350 rad of whole body radiation and then injected with 400 ng pertussels toxin intravenously. Two to three hours later $10 \times 10^6$ 4R3.4 cells, stimulated with MBP(1-13) three days previously, were injected intravenously. These animals were observed twice daily for signs of EAE and mortality. The results of this study are summarized in FIG. 18.

EXAMPLE 5

Down-Regulation of EAE by I-A$^k$-MBP(1-13) Complex

The ability of the I-Ak-MBP(1-13) complex to reverse the course of EAE is examined in the following manner. EAE is induced in A/J female mice with 100 micrograms of MBP(1-13) mixed with complete Freund's adjuvant followed by 200-400 ng of tetanus toxoid administration or by adoptive transfer of 1-10×10$^6$ 4R3.4 T cells into 350 rad irradiated and tetanus toxoid treated B10A(4R) female mice. Two to three days after immunization or as soon as the symptoms of EAE become evident, animals are injected with the complex. The amount and route of administration is determined in preliminary studies, and only those concentrations that are overtly non-toxic are utilized. As an additional control, mice are treated with the complex alone, or with a complex containing an irrelevant antigen. Animals are observed twice daily by two independent observers. Severity of EAE in all groups of mice is graded using a previously described scale, where: 0=no sign of EAE; 1, decreased tail tone only; 2, mild paraparesis; 3, moderately severe paraparesis; 4, complete paraplegia; and 5, moribund.

EXAMPLE 6

EBV Transformation of B Cells from an Individual With an Autoimmune Dysfunction

Peripheral blood mononuclear cells (PBMNC) from an individual with an autoimmune dysfunction are isolated by diluting whole blood or buffy 1:1 with sterile phosphate buffered saline (PBS), pH 7.2, layering the suspension on Ficoll-Hypaque, and centrifuging 20 minutes at 1800-2000 RPM in a table top centrifuge. PBMNC present in a band at the interface of the Ficoll-Hypaque and PBS-plasma are harvested with a pipette and washed twice with PBS. Cells are resuspended at 5×10$^6$ cells/ml in RPMI 1640 containing 10% fetal serum (FBS), plated in a polystyrene flask and incubated for 1 hour at 37° C. to remove monocytes. Non-adherent cells are collected, pelleted by centrifugation and resuspended at 10×10$^6$ cells/ml in Ca$^{}$-Mg$^{}$ free Dulbecco's PBS containing 15% FBS. AET-SRBC (2% v/v) is mixed 1:1 with PBMC, the mixture is centrifuged for 20 min. at 100×g, and then incubated on ice for 1 hour. The pellet is gently resuspended, and the suspension centrifuged through Ficoll-Hypaque as described earlier. The band which contains B cells and remaining monocytes is harvested.

Transformation of B cells is with B95-8 cell line (Walls and Crawford in *Lymphocytes: A Practical Approach* (G. G. B. Klaus ed., IRL Press)). The B95-8 cells are diluted 1:3 in medium, and cultured for 5 days at 37° C. The supernatant is harvested, centrifuged at 250×g for 15 minutes, and filtered through a 0.45 micron millipore filter. The EBV is then concentrated by centrifugation at 10,000 rpm for 2 hours at 4° C., and the pellet containing the virus is suspended in RPMI 1640 containing 10% FBS, at 1% of the original volume.

In order to transform B cells, the virus stock is diluted 1:9 with culture medium containing 2×10$^6$ cells.

After the virus is absorbed to the cells for 1-2 hours at 4° C., the cells are centrifuged at 250×g. The resulting cell pellet is suspended at approximately 0.7×10$^6$ to 7.0×10$^6$ cells/ml in RPMI 1640 containing 10% FBS. Transformed cells are cloned using standard methods.

The transformed B cells made by the procedure are suitable for the isolation of human MHC glycoproteins.

EXAMPLE 7

Elimination of Autoreactive T cell Clones in vitro Using a Complex of Mouse I-A$^k$ and Radiolabeled Rat MBP Peptide This example demonstrates the ability of complexes comprising I-A$^k$ and radiolabeled MBP peptide to selectively kill T cells of desired specificity. The complexes are as described in Example 3, except that the peptide is labeled with $^{131}$I.

The peptide is radiolabeled with $^{131}$I using standard procedures and Iodogen (Pierce, WI). Free $^{131}$I was removed by centrifugation through a Sephadex G-10 column. Affinity purified I-A$^k$ was then incubated with an excess (50-fold) of the labeled peptide at 37° C. for 16 hrs. The unbound peptide was removed by passage through a Sephadex G-10 column in the presence of detergent at a concentration sufficient to prevent aggregation. This preparation was further dialyzed against tissue culture medium to remove detergent and traces of unbound labeled peptide. AJ1.2 T cells were then cultured with different dilutions of this complex for 24 hrs at 37° C. as described above. Following incubation, the cells were washed, incubated with interleukin-2 (IL-2), at a final concentration of 5 U/ml, and the extent of proliferation measured using the MTT spectrophotometric assay as described above.

Two peptides representing amino acids 1-14 of MBP were used. The control radiolabeled peptide had alanine at positions 3, 4 and 6 and tyrosine at position 14. This peptide does not bind AJ1.2 cells. The experimental radiolabeled peptide had alanine at position 4 only and binds AJ1.2 cells.

The results, presented in FIG. 19, show that AJ1.2 cells incubated with 1-A$^k$+$^{131}$I MBP (1-14)A-4 were killed in a dose dependent fashion (heavy cross-hatching in FIG. 7) where as cells incubated with complexes comprising the control peptide were not killed to the same extent (light cross-hatching in FIG. 7). These results demonstrate the ability of the complexes of the present invention to specifically kill a desired T cell clone.

EXAMPLE 8

Elimination of Autoreactive T cell Clones in vitro Using a Complex of 1-A$^k$ and MBP Peptide Conjugated to Adriamycin This example demonstrates in vitro deletion of MBP-specific AJ 1.2 and 4R 3.9 T cells using adriamycin conjugated with MBP(1-14)A4 via an intracellularly cleavable linkage. IA$^k$ was incubated with a 50-fold molar excess of MBP(1-14)A4-Adriamycin conjugate for 24 hrs at 37° C. As an irrelevant control, OVA(3-24-335)-Adriamycin was similarly complexed with IA$^d$. The nonbound peptide-adriamycin conjugates were removed by extensive dialysis against RPMI medium. AJ 1.2 or 4R 3.9 cells were incubated with IA$^d$ or IA$^k$-(peptide-Adriamycin) complex for 16 hrs at 37° C. The cells were washed to remove nonbound complex and plated in culture medium containing IL-2 as described above. After 72 hrs, cell proliferation was measured by the MTT spectrophotometric method as described above.

The peptide-adriamycin conjugates used in the complexes were prepared with an intracellularly cleavable disulfide bond between the peptide and the adriamycin moiety. The preparation of intracellularly cleavable compounds was performed generally as taught in commonly owned copending U.S. patent application Ser. No. 07/513,334, filed May 14, 1990, which is incorporated herein by reference.

The preparation of the conjugates of the present invention was as follows: Doxorubicin hydrochloride (Aldrich Chemical Co., Milwaukee, Wis., 20 mg, 34.4 μmoles) was dissolved in 1 ml dry dimethylsulfoxide (DMSO, Sigma Chemical Co., St. Louis, Mo.) containing 100 μl collidine (Aldrich Chemical Co., 757 μmoles). 2-Iminothiolane (Pierce Chemical Co., Rockford, Ill., 10 mg, 72 μmoles) and 2,2-dithiodipyridine (Aldrich Chemical Co., 75 mg, 340 μmoles) were dissolved in 1 ml dry dimethylsulfoxide. The latter solution was added dropwise with stirring on a Vortex mixer to the doxorubicin solution. After 6 hrs at room temperature and in the dark, the reaction mixture was directly purified by reverse-phase HPLC on a preparative C18 column using linear gradient elution (solvent A: 0.1% aqueous trifluoroacetic (TFA); solvent B: 0.1% TFA in 70% aqueous acetonitrile). Cleavage of the purified product with excess β-merceptoethanol gave the expected products by HPLC analysis. Mass spectroscopy of the purified product confirmed the expected structure.

The HPLC-purified, lyophilized adriamycin-mixed-disulfide derivative (2.3 mg) was dissolved in 0.5 ml degassed water in a 15 ml polypropylene centrifuge tube. HPLC-pure synthetic mercaptopeptide (1 mg) with the structure:

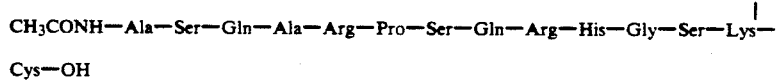

was dissolved in 0.5 ml degassed water and added with vortex mixing to the solution of adriamycin-mixed-disulfide. After 6 hrs at room temperature in the dark, the disulfide linked peptide-adriamycin derivative was purified by gradient elution reverse-phase HPLC on a preparative C18 column, as described above. Reductive cleavage of the disulfide link with excess dithiothreitol gave the expected mercaptopeptide and the 4-mercaptobutyrimidodoxorubicin derivative upon analysis by reverse-phase HPLC. Mass spectroscopy confirmed the structure expected for the peptide-adriamycin derivative.

The HPLC-purified disulfide linked peptide-adriamycin derivative was toxic to cells that internalized the derivative, presumably by intracellular reductive cleavage of the disulfide link with release of the toxic adriamycin moiety.

The results of in vitro T cell deletion with $IA^k$-(peptide-Adriamycin) complex are shown in FIGS. 20A and 20b. About 85% cell deletion of clone AJ 1.2 (No. 4, FIG. 20a) and about 50% deletion of the 4R 3.9 clone (No. 4, FIG. 20b) was achieved at a dose in humans equivalent to about 120 mg of actual $IA^k$-(peptide-Adriamycin) complex (assuming about 20% loading of the $IA^k$ with peptide-Adriamycin) which contains about 1 mg Adriamycin. Adriamycin is administered orally at doses up to 15 mg daily in cancer patients.

EXAMPLE 9

Elimination of Autoreactive T cell Clones in vitro Using a Complex of $IA^k$ and MBP Peptide Conjugated to Mycophenolate In this example complexes similar to those described in Example 8 were demonstrated to selectively kill AJ1.2 T cells. The toxin used in this example was mycophenolate, which blocks the purine synthesis pathway.

100 μg of affinity purified FA was incubated with 167 μg mycophenolic-MBP (1–14) A4 peptide (fifty-fold molar excess) in 1 ml at 37° C. for 8 hrs. The excess unbound peptide was removed as described above and the complex incubated with AJ1.2 cells as described above. Proliferation was measured after 72 by the MTT spectrophotometric assay as described above.

Synthesis of peptide-mycophenolic conjugate was as follows. Mycophenolic acid (Sigma Chemical Co., St. Louis, Mo., 32 mg, 100 μmoles) and bromoacetic acid N-hydroxysuccinimide ester (Sigma Chemical Co., 12 mg, 50 μmoles) were dissolved in 200 μl of dry dimethylsulfoxide (DMSO, Sigma Chemical Co.) containing 9 μl diisopropylethylamine (DIEA, Aldrich Chemical Co., 50 μmoles).

After standing overnight at room temperature, the solution was added with vortex mixing to a solution of 5 mg (2.5 μmoles) of the peptide:

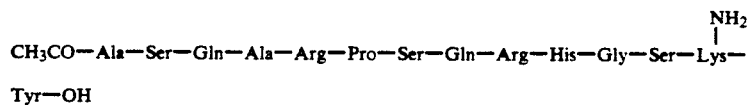

In 100 μL DMSO containing 50 μl DIEA (278 μmoles). After 2 hrs at room temperature, the mycophenoloxyacetylated peptide was precipitated by addition of 50 volumes of dry ethyl acetate (Aldrich Chemical Co.). The peptide derivative was collected by centrifugation, washed several times with ethyl acetate and dried. The dried residue was dissolved in 0.1% TFA and immediately applied to a preparative C18 reverse-phase column. Gradient elution HPLC was used to obtain pure derivative (solvent A: 0.1% aqueous TFA; solvent B: 0.1% TFA in 70% aqueous acetonitrile). The structure of the purified mycophenoloxyacetylated peptide derivative (Attachment at the $N^\epsilon$-amino group of Lys):

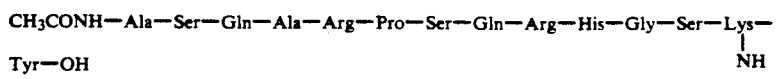

was verified by mass spectroscopy. The HPLC-pure peptide-mycophenolic acid derivative was toxic to cells that internalized the derivative, presumably via intracellular enzymatic hydrolysis of the ester linkage with release of the toxic mycophenolic acid moiety.

The results presented in FIG. 21 show that proliferation of cells incubated with I-A$^k$-MBP(1-14)A4-mycophenolate complexes (No. 3) was significantly less than that of cells alone (No. 1) or cells incubated with unconjugated complexes (No. 2). The results further demonstrate the ability of complexes of the present invention to specifically eliminate particular T cell clones.

Although the foregoing invention has been described in some detail by way of illustration and example for purposes of clarity of understanding, it will be apparent that certain changes and modifications may be practiced within the scope of the appended claims.

What is claimed is:

1. A method for preparing a pharmaceutical composition comprising a pharmaceutically acceptable excipient and a complex capable of binding a T cell receptor, the complex comprising an autoantigenic peptide and an isolated, soluble MHC Class II component having an antigen binding pocket, the method comprising:

isolating the soluble MHC Class II component from a cell capable of producing the component;

contacting the soluble MHC Class II component with the peptide such that the peptide is associated with the antigen binding pocket, thereby forming an MHC Class II-peptide complex;

removing excess peptide not associated with the antigen binding pocket; and mixing the MHC Class II-peptide complex with the pharmaceutically acceptable excipient in a ratio suitable for therapeutic or diagnostic administration of the complex.

2. A method of claim 31 wherein the step of removing excess peptide is carried out by dialysis.

3. A method of claim 1 further comprising the step of covalently linking an effector component to the peptide before the step of contacting the peptide with the MHC component.

4. A method of claim 1 further comprising the step of covalently-linking an effector component to the MHC class II component before the step of contacting the peptide with the MHC component.

5. A method of claim 3 or claim 4 wherein the effector component is a toxin or a label.

6. A method of claim 1 wherein the peptide is nonvalently bound to the antigen-binding pocket.

7. A method of claim 1 wherein the peptide comprises amino acids 1–14 of myelin basic protein.

8. A method of claim 1, wherein the MHC class II component is isolated from spleen cells.

* * * * *

UNITED STATES PATENT AND TRADEMARK OFFICE
CERTIFICATE OF CORRECTION

PATENT NO. : 5,284,935  
DATED : February 8, 1994  
INVENTOR(S) : Clark et al.

Page 1 of 1

It is certified that error appears in the above-identified patent and that said Letters Patent is hereby corrected as shown below:

Column 32, claim 2,
Line 9, please omit the number -- 31 -- and insert the number -- 1 --.

Signed and Sealed this

Twenty-seventh Day of November, 2001

Attest:

*Attesting Officer*

NICHOLAS P. GODICI
*Acting Director of the United States Patent and Trademark Office*